United States Patent
Liot et al.

(10) Patent No.: US 12,187,792 B2
(45) Date of Patent: Jan. 7, 2025

(54) IL-4/IL-13 PATHWAY INHIBITORS FOR ENHANCED EFFICACY IN TREATING CANCER

(71) Applicant: Regeneron Pharmaceuticals, Inc., Tarrytown, NY (US)

(72) Inventors: Caroline Liot, New York, NY (US); Frank Kuhnert, Cortlandt Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 526 days.

(21) Appl. No.: 16/805,481

(22) Filed: Feb. 28, 2020

(65) Prior Publication Data

US 2020/0283518 A1    Sep. 10, 2020

Related U.S. Application Data

(60) Provisional application No. 62/966,760, filed on Jan. 28, 2020, provisional application No. 62/814,648, filed on Mar. 6, 2019.

(51) Int. Cl.
   *A61K 39/395* (2006.01)
   *A61K 39/00* (2006.01)
   (Continued)

(52) U.S. Cl.
   CPC ........ *C07K 16/247* (2013.01); *A61K 39/3955* (2013.01); *A61K 39/4636* (2023.05);
   (Continued)

(58) Field of Classification Search
   CPC .. A61K 39/395; A61K 39/3955; C07K 16/28; C07K 16/2866
   See application file for complete search history.

(56) References Cited

U.S. PATENT DOCUMENTS 6,808,710 B1  10/2004  Wood et al.
7,488,802 B2   2/2009  Collins et al.
   (Continued)

FOREIGN PATENT DOCUMENTS

EP    3177649 A1   6/2017
EP    2627673 B1   7/2017
   (Continued)

OTHER PUBLICATIONS

Prokopchuk et al. Interleukin-4 enhances proliferation of human pancreatic cancer cells: evidence for autocrine and paracrine actions. British Journal of Cancer (2005) 92, 921-928 (Year: 2005).*
   (Continued)

*Primary Examiner* — Xiaozhen Xie
(74) *Attorney, Agent, or Firm* — Fox Rothschild LLP; Aparna G. Patankar

(57) ABSTRACT

The disclosure relates to methods for treating or inhibiting the growth of a tumor, wherein the methods include selecting and administering to a subject in need thereof a therapeutically effective amount of an IL-4/IL-13 pathway inhibitor and a therapeutically effective amount of a programmed death 1 (PD-1) inhibitor. In certain embodiments, the IL-4/IL-13 pathway inhibitor enhances the anti-tumor efficacy of PD-1 blockade.

40 Claims, 6 Drawing Sheets

Specification includes a Sequence Listing.

(51) Int. Cl.
  *A61K 45/06* (2006.01)
  *A61P 35/00* (2006.01)
  *C07K 16/24* (2006.01)
  *C07K 16/28* (2006.01)
(52) U.S. Cl.
  CPC .............. *A61K 45/06* (2013.01); *A61P 35/00* (2018.01); *C07K 16/244* (2013.01); *C07K 16/28* (2013.01); *C07K 16/2818* (2013.01); *C07K 16/2866* (2013.01)

(56) References Cited

U.S. PATENT DOCUMENTS

| | | | |
|---|---|---|---|
| 7,501,121 | B2 | 3/2009 | Tchistiakova et al. |
| 7,638,606 | B2 | 12/2009 | Carter et al. |
| 7,674,459 | B2 | 3/2010 | Fung et al. |
| 7,740,843 | B2 | 6/2010 | Carballido Herrera et al. |
| 7,807,788 | B2 | 10/2010 | Ashman et al. |
| 7,910,708 | B2 | 3/2011 | Campbell et al. |
| 7,915,388 | B2 | 3/2011 | Wu et al. |
| 7,935,343 | B2 | 5/2011 | Monk et al. |
| 7,943,743 | B2 | 5/2011 | Korman et al. |
| 8,008,449 | B2 | 8/2011 | Korman et al. |
| 8,088,618 | B2 | 1/2012 | Fung et al. |
| 8,092,804 | B2 | 1/2012 | Eriksson et al. |
| 8,168,757 | B2 | 5/2012 | Finnefrock et al. |
| 8,217,149 | B2 | 7/2012 | Irving et al. |
| 8,354,509 | B2 | 1/2013 | Carven et al. |
| 8,388,965 | B2 | 3/2013 | Rao et al. |
| 8,609,089 | B2 | 12/2013 | Langermann et al. |
| 8,679,487 | B2 | 3/2014 | Armitage et al. |
| 8,686,119 | B2 | 4/2014 | Rotem-Yehudar et al. |
| 8,691,233 | B2 | 4/2014 | Gozzard et al. |
| 8,779,105 | B2 | 7/2014 | Korman et al. |
| 8,877,189 | B2 | 11/2014 | Eriksson et al. |
| 8,900,587 | B2 | 12/2014 | Carven et al. |
| 9,308,236 | B2 | 4/2016 | Miller et al. |
| 9,402,899 | B2 | 8/2016 | Honjo et al. |
| 9,574,004 | B2 * | 2/2017 | Ardeleanu ......... A61K 39/3955 |
| 9,587,026 | B2 | 3/2017 | Armitage et al. |
| 9,605,065 | B2 | 3/2017 | Fung et al. |
| 9,624,298 | B2 | 4/2017 | Nastri et al. |
| 9,938,345 | B2 | 4/2018 | Papadopoulos et al. |
| 9,987,500 | B2 | 6/2018 | Papadopoulos et al. |
| 10,011,656 | B2 | 7/2018 | Freeman et al. |
| 2006/0073148 | A1 | 4/2006 | Tchistiakova et al. |
| 2008/0044420 | A1 | 2/2008 | Heavner et al. |
| 2010/0297110 | A1 | 11/2010 | Hoeger et al. |
| 2011/0008345 | A1 | 1/2011 | Ashman et al. |
| 2013/0251718 | A1 | 9/2013 | Rao et al. |
| 2015/0017182 | A1 * | 1/2015 | Mannent ................. A61P 11/02 424/158.1 |
| 2015/0203579 | A1 * | 7/2015 | Papadopoulos ........... A61P 7/04 600/1 |
| 2016/0207995 | A1 | 7/2016 | Yansura et al. |
| 2017/0239342 | A1 * | 8/2017 | Purcell Ngambo ..... A61P 11/14 |
| 2017/0290808 | A1 | 10/2017 | Charo et al. |
| 2019/0048096 | A1 * | 2/2019 | Hermann ................ A61P 35/00 |

FOREIGN PATENT DOCUMENTS

| | | |
|---|---|---|
| WO | 2006/121168 A1 | 11/2006 |
| WO | 2007/005874 A2 | 1/2007 |
| WO | 2009/114335 A2 | 9/2009 |
| WO | 2010/077634 A1 | 7/2010 |
| WO | 2012047954 A1 | 4/2012 |
| WO | 2013/181452 A1 | 12/2013 |
| WO | 2013/181634 A2 | 12/2013 |
| WO | 2015112805 A1 | 7/2015 |
| WO | 2016/149201 A2 | 9/2016 |
| WO | 2017011580 A2 | 1/2017 |
| WO | 2017/034916 A1 | 3/2017 |
| WO | 2018156494 A1 | 8/2018 |
| WO | 2019/051204 A1 | 3/2019 |

OTHER PUBLICATIONS

Feng et al. PD-1/PD-L1 and immunotherapy for pancreatic cancer. Cancer Letters 407 (2017) 57-65 (Year: 2017).*
Provenzano et al. Enzymatic targeting of the stroma ablates physical barriers to treatment of pancreatic ductal adenocarcinoma. Cancer Cell. Mar. 20, 2012; 21(3): 418-429 (Year: 2012).*
Piro et al (A circulating TH2 cytokines profile predicts survival in patients with resectable pancreatic adenocarcinoma Oncoimmunology (2017) 6(9):e1322242) (Year: 2017).*
Salman et al (Vaccine Therapy for Pancreatic Cancer Oncolmmunology (2013) 2(12):e26662) (Year: 2013).*
Long et al., J. Allergy Clin. Immunol., 2014, vol. 134(3):560-567.*
Corren et al., "A randomized, controlled, Phase 2 study of AMG 317, an IL-4Ralpha antagonist, in patients with asthma", Am J Respir Crit Care Med., (2010) 181(8):788-796. (abstract).
De Monte et al., "Intratumor T Helper Type 2 Cell Infiltrate Correlates With Cancer-Associated Fibroblast Thymic Stromal Lymphopoietin Production and Reduced Survival in Pancreatic Cancer", J Exp Med, (2011) 208(3):469-78.
De Monte et al., "Basophil Recruitment into Tumor-Draining Lymph Nodes Correlates with Th2 Inflammation and Reduced Survival in Pancreatic Cancer Patients", Cancer Research, (2016) 76(7), 1792-1803.
Denardo et al., "CD4(+) T Cells Regulate Pulmonary Metastasis of Mammary Carcinomas by Enhancing Protumor Properties of Macrophages", Cancer Cell, (2009) 16(2):91-102.
Dey et al. "Oncogenic KRAS-Driven Metabolic Reprogramming in Pancreatic Cancer Cells Utilizes Cytokines from the Tumor Microenvironment", Cancer Discovery, (2020) 10(4), 608-625. (abstract).
Feig et al., "Targeting CXCL12 from FAP-expressing carcinoma-associated fibroblasts synergizes with anti-PD-L1 Immunotherapy in pancreatic cancer", Proc Natl Acad Sci U S A., (2013) 110(50):20212-17.
Formentini et al., "Expression of interleukin-4 and interleukin-13 and Their Receptors in Colorectal Cancer", Int J Colorectal Dis., (2012) 27(10):1369-76. (abstract).
Gieseck et al., "Type 2 Immunity in Tissue Repair and Fibrosis", Nat Rev Immunol., (2017) 18(1):62-76.
Gorelik et al., "Abstract 4606: Preclinical characterization of a novel fully human IgG1 anti-PD-L1 mAb CK-301" In: Proceedings of the American Association for Cancer Research Annual Meeting 2017; Apr. 1-5, 2017; Washington, DC. Philadelphia (PA): AACR. (abstract).
Ito et al. "IL-4 blockade alters the tumor microenvironment and augments the response to cancer immunotherapy in a mouse model", Cancer Immunology, Immunotherapy, (2017) 66(11), 1485-1496.
Jacobetz et al., "Hyaluronan Impairs Vascular Function and Drug Delivery in a Mouse Model of Pancreatic Cancer" Gut, (2013) 62(1):112-20.
Joshi et al., "Interleukin-4 Receptor Alpha Overexpression in Human Bladder Cancer Correlates With the Pathological Grade and Stage of the Disease", Cancer Med., (2014) 3(6):1615-28.
Kazane et al., "Self-Assembled Antibody Multimers through Peptide Nucleic Acid Conjugation", J. Am. Chem. Soc., (2013) 135(1):340-46. (abstract).
Klein et al., "Progress in Overcoming the Chain Association Issue in Bispecific Heterodimeric IgG Antibodies", mAbs (2012) 4(6):653-663.
Langer, "New methods of drug delivery", Science (1990) 249:1527-1533. (abstract).
Liou et al. "The Presence of Interleukin-13 at Pancreatic ADM/PanIN Lesions Alters Macrophage Populations and Mediates Pancreatic Tumorigenesis", CellReports, (2017) 19(7), 1322-1333.
Maier et al., "A conserved dendritic-cell regulatory program limits antitumour immunity", Nature Publishing Group, (2020) pp. 1-21. (abstract).
Olive et al., "Inhibition of Hedgehog Signaling Enhances Delivery of Chemotherapy in a Mouse Model of Pancreatic Cancer", Science, (2009) 324(5933):1457-61.
Ostrand-Rosenberg et al. "Cutting edge: STAT6-deficient mice have enhanced tumor immunity to primary and metastatic mammary

(56) References Cited

OTHER PUBLICATIONS carcinoma", The Journal of Immunology, (2000) 165(11), 6015-6019.
Pedroza-Gonzalez et al., "Thymic Stromal Lymphopoietin Fosters Human Breast Tumor Growth by Promoting Type 2 Inflammation", J Exp Med, (2011) 208(3):479-90.
Piro et al., "A Circulating T H 2 Cytokines Profile Predicts Survival in Patients With Resectable Pancreatic Adenocarcinoma", Oncoimmunology (2017) 6(9): e1322242.
Powell et al., "Compendium of Excipients for Parenteral Formulations", J Pharm Sci Technol, (1998) 52:238-311.
Prokopchuk et al., "Interleukin-4 enhances proliferation of human pancreatic cancer cells: evidence for autocrine and paracrine actions", British Journal of Cancer, (2005) 92(5), 921-928.
Provenzano et al., "Enzymatic Targeting of the Stroma Ablates Physical Barriers to Treatment of Pancreatic Ductal Adenocarcinoma", Cancer Cell, (2012) 21(3):418-29.
Taylor et al., "A transgenic mouse that expresses a diversity of human sequence heavy and light chain Immunoglobulins", Nucl. Acids Res., (1992) 20:6287-6295.
Tong et al., "Interleukin-33 Predicts Poor Prognosis and Promotes Ovarian Cancer Cell Growth and Metastasis Through Regulating ERK and JNK Signaling Pathways", Mol Oncol., (2015) 10(1):113-25.
Valenzuela et al., "High-throughput Engineering of the Mouse Genome Coupled With High-Resolution Expression Analysis", Nat. Biotechnol. (2003) 21:652-659. (abstract).
Venmar et al., "IL4 receptor a mediates enhanced glucose and glutamine metabolism to support breast cancer growth", Biochim Biophys Acta, (2015) 1853(5):1219-28.
Wu et al., "Receptor-mediated in Vitro Gene Transformation by a Soluble DNA Carrier System", J. Biol. Chem., (1987) 262: 4429-4432.
Wynn, "Type 2 cytokines: mechanisms and therapeutic strategies", Nat Rev Immunol., (2015) 15(5):271-82. (abstract).
Zhang et al., "Structural basis of a novel PD-L1 nanobody for immune checkpoint blockade", Cell Discovery, (Mar. 2017) 3, 170004.
Internatioanl Search Report and Written Opinion mailed Jun. 26, 2020 in PCT/US2020/020494.
Pu et al., "PD-1 Immunotherapy in Pancreatic Cancer: Current Status," J. of Pancreatology, 2(1):6-10 (Mar. 1, 2019).
Bankaitis et al., "Targeting IL4/IL4R for the Treatment of Epithelial Cancer Metastasis," Clin. and Exper. Matastasis, Springer Netherlands, NL, 32(8):847-856 (Sep. 18, 2015).
Van Audenaerde et al., "PO-417? Anti-Tumoral Effects of IL-15 and CD40 Stimulation as a Novel Combination Immunotherapy for Pancreatic Cancer," Poster Presentation, Jun. 29, 2018, pp. A393.2-A394.
Gray et al., "Phosphatidylserine-targeting antibodies augment the anti-tumorigenic activity of anti-PD-1 therapy by enhancing immune activation and downregulating pro-oncogenic factors induced by T-cell checkpoint inhibition in murine triple-negative breast cancers", Breast Cancer Research (2016), 18 (Art. 50): 1-14.
Seufferlein et al., "More than a Gel—Hyaluronic Acid, a Central Component in the Microenvironment of Pancreatic Cancer", European Oncology & Haematology (2018), 14(1): 40-44.
Pu et al., "PD-1 immunotherapy in pancreatic cancer: current status," J Pancreatology (2019), 2(1): 6-10.
Bankaitis et al., "Targeting IL4/IL4R for the treatment of epithelial cancer metastasis," Clin Exp Metastasis (2015), 32(8): 847-56.
Badri et al., "Optimization of radiation dosing schedules for proneural glioblastoma," J Math Bio (2016), 72(5): 1301-1336.
Baylot et al., "TCTP Has a Crucial Role in the Different Stages of Prostate Cancer Malignant Progression," Results Probl Cell Differ (2017), 64: 255-61.
Wolchok, "Putting the Immunologic Brakes on Cancer," Cell (2018), 175: 1452-54.
Setrerrahmane et al., "Tumor-related interleukins: old validated targets for new anti-cancer drug development," Molecular Cancer (2017) 16: 153 (17 pp).

* cited by examiner

IL-4/IL-13 PATHWAY INHIBITORS FOR ENHANCED EFFICACY IN TREATING CANCER

CROSS REFERENCE TO RELATED APPLICATION

This application claims the benefit of priority to U.S. Provisional Patent Application 62/814,648 filed Mar. 6, 2019, and U.S. Provisional Patent Application 62/966,760 filed Jan. 28, 2020, the disclosures of all of which are hereby incorporated herein by reference in their entireties.

FIELD OF THE INVENTION

The present disclosure relates to methods for treating cancer comprising administering to a subject in need thereof a therapeutically effective amount of an IL-4/IL-13 pathway inhibitor in combination with a therapeutically effective amount of a programmed death 1 (PD-1) inhibitor. In certain embodiments, the IL-4/IL-13 pathway inhibitor enhances the anti-tumor efficacy of PD-1 blockade.

BACKGROUND

Type 2 immunity promotes tumor growth and metastasis in various cancer types. Several Type 2-associated cytokines, chemokines or receptors have been implicated in cancer, and are overexpressed in various human tumors. For instance, IL-4, IL-13, IL-4Rα, and IL-33 are overexpressed in a number of human cancer types, and are associated with poor prognosis in bladder, breast or ovarian cancer (Joshi et al., Cancer Med., 3(6):1615-28, 2014; Formentini et al., Int J Colorectal Dis., 27(10):1369-76, 2012); Tong et al., Mol Oncol. 10(1):113-25, 2015). Type 2 immunity is characterized by the production of a number of Type 2 cytokines and chemokines (e.g., IL-4, IL-13, thymic stromal lymphopoietin (TSLP), IL-33) and is commonly observed in tissues during allergic responses or anti-parasitic infections. A Type 2 immune response also contributes to tissue repair response and fibrosis (Wynn, Nat Rev Immunol., 15(5):271-82, 2015; Gieseck et al., Nat Rev Immunol., 18(1):62-76, 2017).

Pancreatic Ductal Adenocarcinoma (PDAC) is the third leading cause of cancer-related death in the US, with a 5-year survival rate of 8%. This extremely poor prognosis is largely because PDAC is refractory to most therapies. In particular, immune checkpoint blockade (ICB) immunotherapy (e.g., anti-PD-1 or anti-cytotoxic T-lymphocyte-associated protein 4 (CTLA-4)) has failed to provide a clinical response in PDAC patients. A key contributor to the strong drug resistance in PDAC is its unique desmoplastic stroma—a dense fibrotic and stromal reaction consisting of cancer-associated fibroblasts, immune cells and large amounts of extra-cellular matrix components—which acts as a physical barrier to drug perfusion and T cell infiltration, and creates a profoundly immunosuppressive environment that inhibits T cell function (Olive et al., Science, 324(5933): 1457-61, 2009; Provenzano et al., Cancer Cell, 21(3):418-29, 2012; Feig et al., Proc Natl Acad Sci USA., 110(50): 20212-17, 2013).

Preclinical studies have shown that genetic ablation or blockade of IL-13, IL-4R, or TSLP can decrease tumor growth and metastasis burden in pancreatic, breast and colorectal cancer. Additionally, serum IL-4 and TSLP were shown to predict survival in pancreatic cancer patients (Piro et al., Oncoimmunology 6(9): e1322242, 2017; De Monte et al., J Exp Med, 208(3):469-78, 2011). Mechanisms of Type 2 immunity-dependent tumorigenesis include induction of fibrosis formation, inhibition of anti-tumor surveillance or increased glucose and glutamine cancer cell metabolism (DeNardo et al., Cancer Cell, 16(2):91-102, 2009; Liou et al, Cell Rep., 19(7):1322-33, 2017; Pedroza-Gonzalez et al., J Exp Med, 208(3):479-90, 2011; Venmar et al., Biochim Biophys Acta, 1853(5):1219-28, 2015; Ostrand-Rosenberg et al., J. Immunol., 165:6015-19, 2000). Collectively, these data demonstrate that Type 2 immunity promotes tumor growth and metastasis in various cancer types.

Thus, there is a need for new and effective therapies to treat cancer, including cancers and cancer type subsets, characterized by Type 2 immune response and cancers that are resistant to prior therapy.

SUMMARY

In one aspect, the disclosed technology relates to a method of treating or inhibiting the growth of a tumor, including: (a) selecting a subject with a tumor; and (b) administering to the subject in need thereof a therapeutically effective amount of an IL-4/IL-13 pathway inhibitor and a therapeutically effective amount of a programmed death 1 (PD-1) inhibitor. In one embodiment, the subject has a tumor selected from the group consisting of colorectal cancer, ovarian cancer, prostate cancer, bladder cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, myeloma, Hodgkin's lymphoma, non-Hodgkin's lymphoma, follicular lymphoma, small lymphocytic lymphoma, lymphoplasmacytoid lymphoma, marginal zone lymphoma, mantle cell lymphoma, diffuse large B-cell lymphoma, B-cell lymphomas, lymphomatoid granulomatosis, Burkitt's lymphoma, acute lymphoblastic leukemia, hairy cell leukemia, and B cell chronic lymphocytic leukemia. In one embodiment, the tumor includes a Type 2 immunity-dependent cancer. In another embodiment, the Type 2 immunity-dependent cancer includes pancreatic cancer, breast cancer, colorectal cancer, ovarian cancer, brain cancer, skin cancer, prostate cancer, kidney cancer, lung cancer, Hodgkin's lymphoma or bladder cancer. In another embodiment, the tumor includes pancreatic cancer. In one embodiment, the tumor is primary, metastatic or recurrent. In one embodiment, the subject has been treated with one or more anti-cancer therapies. In one embodiment, the subject has a tumor that is resistant or inadequately responsive to prior therapy. In one embodiment, the subject has a tumor that resistant or non-responsive to treatment with an immune checkpoint inhibitor (e.g., a PD-1 inhibitor, a LAG3 inhibitor, etc.).

In one embodiment, the IL-4/IL-13 pathway inhibitor is selected from the group consisting of an anti-IL-4 antibody, an anti-IL-13 antibody, an anti-IL-4/IL-13 bispecific antibody, an IL-4 receptor (IL-4R) inhibitor, an IL-4 trap, an IL-13 trap, and an anti-IL-4R antibody. In another embodiment, the IL-4/IL-13 pathway inhibitor is an anti-IL-4 antibody (e.g., pascolizumab). In another embodiment, the IL-4/IL-13 pathway inhibitor is an anti-IL-13 antibody (e.g., tralokinumab, lebrikizumab, dectrekumab, GSK679586, or MED17836). In another embodiment, the IL-4/IL-13 pathway inhibitor is an anti-IL-4/IL-13 bispecific antibody (e.g., romilkimab). In another embodiment, the IL-4/IL-13 pathway inhibitor is an IL-4R inhibitor (e.g., an IL-4 mutein such as pitrakinra or an anti-IL-4R antibody). In another embodiment, the IL-4/IL-13 pathway inhibitor is an anti-IL-4R antibody. In another embodiment, the IL-4/IL-13 pathway inhibitor is an IL-4 or IL-13 trap.

In another embodiment, the anti-IL-4R antibody includes a heavy chain variable region (HCVR) including the amino acid sequence of SEQ ID NO: 1 and a light chain variable region (LCVR) including the amino acid sequence of SEQ ID NO: 2. In another embodiment, the HCVR includes three heavy chain complementarity determining regions (CDRs) (HCDR1, HCDR2 and HCDR3) and the LCVR includes three light chain CDRs (LCDR1, LCDR2 and LCDR3), wherein: HCDR1 has an amino acid sequence of SEQ ID NO: 3; HCDR2 has an amino acid sequence of SEQ ID NO: 4; HCDR3 has an amino acid sequence of SEQ ID NO: 5; LCDR1 has an amino acid sequence of SEQ ID NO: 6; LCDR2 has an amino acid sequence of SEQ ID NO: 7; and LCDR3 has an amino acid sequence of SEQ ID NO: 8. In another embodiment, the anti-IL-4R antibody includes a heavy chain and a light chain, wherein the heavy chain has an amino acid sequence of SEQ ID NO: 9. In another embodiment, the anti-IL-4R antibody includes a heavy chain and a light chain, wherein the light chain has an amino acid sequence of SEQ ID NO: 10. In another embodiment, the anti-IL-4R antibody includes a heavy chain and a light chain, wherein the heavy chain has an amino acid sequence of SEQ ID NO: 9 and the light chain has an amino acid sequence of SEQ ID NO: 10. In another embodiment, the IL-4/IL-13 pathway inhibitor is dupilumab or a bioequivalent thereof. In another embodiment, the IL-4/IL-13 pathway inhibitor is selected from the group consisting of dupilumab, pascolizumab, AMG317, MED12045, MEDI9314, tralokinumab, lebrikzimab, anrukinzumab, dectrekumab, GSK679586, MED17836, romilkimab, an IL-4 trap, an IL-13 trap, AER-003, and pitrakinra.

In one embodiment, the PD-1 inhibitor is selected from an anti-PD-1 antibody, an anti-PD-L1 antibody, and an anti-PD-L2 antibody. In another embodiment, the PD-1 inhibitor is an anti-PD-1 antibody that includes a HCVR including the amino acid sequence of SEQ ID NO: 11 and a LCVR including the amino acid sequence of SEQ ID NO: 12. In another embodiment, the HCVR includes three heavy chain CDRs (HCDR1, HCDR2 and HCDR3) and the LCVR includes three light chain CDRs (LCDR1, LCDR2 and LCDR3), wherein: HCDR1 has an amino acid sequence of SEQ ID NO: 13; HCDR2 has an amino acid sequence of SEQ ID NO: 14; HCDR3 has an amino acid sequence of SEQ ID NO: 15; LCDR1 has an amino acid sequence of SEQ ID NO: 16; LCDR2 has an amino acid sequence of SEQ ID NO: 17; and LCDR3 has an amino acid sequence of SEQ ID NO: 18. In another embodiment, the anti-PD-1 antibody includes a HCVR/LCVR sequence pair of SEQ ID NOs: 11/12. In another embodiment, the anti-PD-1 antibody includes a heavy chain and a light chain, wherein the heavy chain has an amino acid sequence of SEQ ID NO: 19. In another embodiment, the anti-PD-1 antibody includes a heavy chain and a light chain, wherein the light chain has an amino acid sequence of SEQ ID NO: 20. In another embodiment, the anti-PD-1 antibody includes a heavy chain and a light chain, wherein the heavy chain has an amino acid sequence of SEQ ID NO: 19 and the light chain has an amino acid sequence of SEQ ID NO: 20. In another embodiment, the PD-1 inhibitor is cemiplimab or a bioequivalent thereof. In another embodiment, the PD-1 inhibitor is an anti-PD-1 antibody selected from the group consisting of cemiplimab, nivolumab, pembrolizumab, pidilizumab, MEDI0608, BI 754091, PF-06801591, sintilimab, AGEN2034, spartalizumab, camrelizumab, JNJ-63723283, and MCLA-134. In another embodiment, the PD-1 inhibitor is an anti-PD-L1 antibody selected from the group consisting of H1H8314N, avelumab, atezolizumab, durvalumab, MDX-1105, LY3300054, FAZ053, STI-1014, CX-072, KN035, and CK-301.

In another embodiment, one or more doses of the IL-4/IL-13 pathway inhibitor are administered in combination with one or more doses of the anti-PD-1 antibody. In another embodiment, at least one dose of the IL-4/IL-13 pathway inhibitor includes about 0.1 to about 50 mg/kg of the subject's body weight. In another embodiment, at least one dose of the IL-4/IL-13 pathway inhibitor includes about 0.05 to about 1000 mg of the inhibitor. In another embodiment, at least one dose of the PD-1 inhibitor includes about 0.1 mg/kg to about 20 mg/kg of the subject's body weight. In another embodiment, at least one dose of the PD-1 inhibitor includes about 0.05 to about 500 mg of the inhibitor. In another embodiment, the IL-4/IL-13 pathway inhibitor is administered prior to the PD-1 inhibitor. In another embodiment, the IL-4/IL-13 pathway inhibitor is administered after the PD-1 inhibitor. In another embodiment, the IL-4/IL-13 pathway inhibitor is administered concurrently with the PD-1 inhibitor. In another embodiment, the method promotes tumor regression, delays tumor growth, reduces tumor cell load, reduces tumor burden, and/or prevents tumor recurrence in the patient. In another embodiment, the method promotes at least about 10% more tumor regression in the treated subject as compared to an untreated subject or a subject treated with either inhibitor as monotherapy. In another embodiment, the method leads to at least 30% or more decrease in tumor cells or tumor size as compared to an untreated subject or a subject treated with either inhibitor as monotherapy.

In another embodiment, the method further includes administering at least one additional therapeutic agent or therapy. In another embodiment, the additional therapeutic agent or therapy includes chemotherapy, cyclophosphamide, surgery, radiation, a cancer vaccine, a LAG3 inhibitor, a CTLA-4 inhibitor, a GITR agonist, a TIM3 inhibitor, a BTLA inhibitor, a TIGIT inhibitor, a CD47 inhibitor, an IDO inhibitor, a VEGF antagonist, an Ang2 inhibitor, a TGF3 inhibitor, an EGFR inhibitor, a VISTA inhibitor, a CD38 inhibitor, a CD40 agonist, a CSF1R inhibitor, CCR2 inhibitor, CXCR4 inhibitor, CXCR2 inhibitor, CCR4 inhibitor, CXCL12 inhibitor, a CD28 activator, an agonist to a co-stimulatory receptor, an antibody to a tumor-specific antigen, an anti-CD3/anti-CD20 bispecific antibody, GM-CSF, a cytotoxin, a chemotherapeutic agent, an oncolytic virus, an IL-6R inhibitor, an IL-10 inhibitor, a cytokine or a derivative thereof (e.g., IL-12 or IL-2), an ADC, chimeric antigen receptor T cells, an anti-inflammatory drug, a NSAID, and/or a dietary supplement.

In another aspect, the disclosed technology relates to a pharmaceutical delivery system including: (a) a pharmaceutical composition including an IL-4/IL-13 pathway inhibitor and a pharmaceutically acceptable carrier; and (b) a pharmaceutical composition including a programmed death 1 (PD-1) inhibitor and a pharmaceutically acceptable carrier. In one embodiment, the pharmaceutical compositions (a) and (b) are separate from each other. In another embodiment, the pharmaceutical composition (a) includes one or more doses of the IL-4/IL-13 pathway inhibitor. In another embodiment, the at least one dose includes about 5-1000 mg of the IL-4/IL-13 pathway inhibitor. In another embodiment, the pharmaceutical composition (b) includes one or more doses of the PD-1 inhibitor. In another embodiment, the at least one dose includes about 5-500 mg of the PD-1 inhibitor. In another embodiment, the IL-4/IL-13 pathway inhibitor is selected from the group consisting of an anti-IL-4 antibody, an anti-IL-13 antibody, an anti-IL-4/IL-13 bispecific antibody, an IL-4 receptor (IL-4R) inhibitor, an IL-4 trap, an IL-13 trap, and an anti-IL-4R antibody. In another embodiment, the IL-4/IL-13 pathway inhibitor is selected from the group consisting of dupilumab, pascolizumab, AMG317, MEDI2045, MEDI9314, tralokinumab, lebrikzimab, anrukinzumab, dectrekumab, GSK679586, MEDI7836, romilkimab, an IL-4 trap, an IL-13 trap, AER-003, and pitrakinra. In another embodiment, the PD-1 inhibitor is selected from the group consisting of an anti-PD-1 antibody, an anti-PD-L1 antibody, and an anti-PD-L2 antibody. In another embodiment, the PD-1 inhibitor is an anti-PD-1 antibody selected from the group consisting of cemiplimab, nivolumab, pembrolizumab, pidilizumab, MEDI0608, BI 754091, PF-06801591, sintilimab, AGEN2034, spartalizumab, camrelizumab, JNJ-63723283, and MCLA-134. In another embodiment, the PD-1 inhibitor is an anti-PD-L1 antibody selected from the group consisting of H1H8314N, avelumab, atezolizumab, durvalumab, MDX-1105, LY3300054, FAZ053, STI-1014, CX-072, KN035, and CK-301.

In another embodiment, the pharmaceutical delivery system further includes at least one additional therapeutic agent selected from the group consisting of cyclophosphamide, a cancer vaccine, a LAG3 inhibitor, a CTLA-4 inhibitor, a GITR agonist, a CD28 activator, a TIM3 inhibitor, a BTLA inhibitor, a TIGIT inhibitor, a CD38 inhibitor, a CD47 inhibitor, an IDO inhibitor, a VEGF antagonist, an Ang2 inhibitor, a TGFβ inhibitor, an EGFR inhibitor, a VISTA inhibitor, a CD40 agonist, a CSF1R inhibitor, CCR2 inhibitor, CXCR4 inhibitor, CXCR2 inhibitor, CCR4 inhibitor, CXCL12 inhibitor, an agonist to a co-stimulatory receptor, an antibody to a tumor-specific antigen, an anti-CD3/anti-CD20 bispecific antibody, GM-CSF, a cytotoxin, a chemotherapeutic agent, an IL-6R inhibitor, an IL-10 inhibitor, an oncolytic virus, a cytokine, an ADC, chimeric antigen receptor T cells, an anti-inflammatory drug, a NSAID, and a dietary supplement. In another embodiment, the pharmaceutical delivery system is for use in treating or inhibiting the growth of a tumor. In another embodiment, the tumor includes a Type 2 immunity-dependent cancer.

In another aspect, the disclosed technology relates to a kit including a pharmaceutical delivery system having: (a) a pharmaceutical composition including an IL-4/IL-13 pathway inhibitor and a pharmaceutically acceptable carrier; (b) a pharmaceutical composition including a PD-1 inhibitor and a pharmaceutically acceptable carrier; and written instructions for use of the IL-4/IL-13 pathway inhibitor in combination with the PD-1 inhibitor for treating or inhibiting the growth of a tumor.

In another aspect, the disclosed technology relates to an IL-4/IL-13 pathway inhibitor for use in a method of treating or inhibiting the growth of a tumor in combination a PD-1 inhibitor, said method including administering to a subject in need thereof a therapeutically effective amount of each inhibitor. In another aspect, the disclosed technology relates to a PD-1 inhibitor for use in a method of treating or inhibiting the growth of a tumor in combination a IL-4/IL-13 pathway inhibitor, said method including administering to a subject in need thereof a therapeutically effective amount of each inhibitor.

DETAILED DESCRIPTION

Figure 1A:
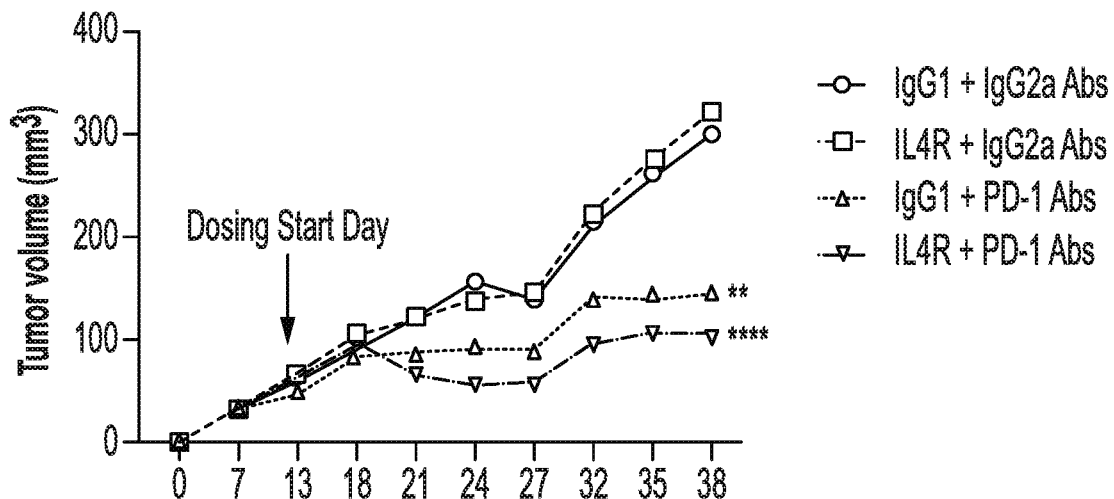
FIG. 1A is a line graph showing tumor volume reduction from 30-110 mm$^3$ tumor volumes at baseline in accordance with the study described in Example 1. The asterisks (*) indicate degree of statistical significance relative to isotype controls (IgGs).

It is to be understood that the present disclosure is not limited to the particular methods and experimental conditions described, as such methods and conditions may vary. It is also to be understood that the terminology used herein is for the purpose of describing particular embodiments only, and is not intended to be limiting, and that the scope of the present disclosure will be limited only by the appended claims.

Unless defined otherwise, all technical and scientific terms used herein have the same meaning as commonly understood by one of ordinary skill in the art to which the disclosed invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present disclosure, the preferred methods and materials are now described.

The present disclosure includes methods for treating cancer comprising administering to a subject in need thereof a therapeutically effective amount of an IL-4/IL-13 pathway inhibitor in combination with a therapeutically effective amount of a programmed death 1 (PD-1) inhibitor. In some embodiments, the disclosed methods target Type 2 immunity-dependent pro-tumorigenic mechanisms in cancers, thus providing a new and highly effective method for treating or inhibiting the growth of tumors, including those that exhibit desmoplastic features. In some embodiments, the disclosed methods treat Type 2 immunity-dependent cancers using IL-4R blockade or other immunotherapies targeting Type 2 immune response pathways, in combination with anti-tumor agents, including but not limited to ICBs (e.g., chemotherapy, bispecific antibodies, antibody drug conjugates (ADCs), and Chimeric Antigen Receptor (CAR) T-cells).

As used herein, "Type 2 immunity gene signature" refers to the upregulation or overexpression of one or more Type 2 cytokines, Type 2 chemokines, Type 2 receptors, and Type 2-downstream target genes, including but not limited to: IL-13RA2, IL25, IL17RB, SERPINB2, CCL24, CEACAM1, CCL1, MUC5B, CCL26, IL-13RA1, POSTN, IL6R, CCL18, CCL17, FCER2, CCR3, IL6, CCL8, CRLF2, IL33, TSLP, IL-4R, CCR4, PTGDR, FCER1A, IL1 RL1, DPP4, IL-4, IL5, and IL-13. As demonstrated in Example 3, for instance, IL-4 and IL-13 gene expression were found to be massively upregulated in an in vivo model of pancreatic cancer, a Type 2 immunity-dependent cancer.

As used herein, "Type 2 immunity-dependent cancers" refers to cancers or subsets of cancers, such as human cancers or subsets of human cancers, showing a strong Type 2 immunity gene signature.

As used herein, "Type 2 immunity pathway blockade" refers to immunotherapy targeting any gene of the Type 2 immunity gene signature.

Methods of Treating or Inhibiting Growth of a Tumor

The present disclosure includes methods for treating, ameliorating, or reducing the severity of at least one symptom or indication, or inhibiting the growth of a cancer in a subject. In this aspect, the disclosed methods include selecting a subject with a tumor and administering to the subject in need thereof a therapeutically effective amount of an IL-4/IL-13 pathway inhibitor (e.g., an anti-IL-4 antibody, an anti-IL-13 antibody, an anti-IL-4/IL-13 bispecific antibody, an IL-4 receptor (IL-4R) inhibitor, an anti-IL-4R antibody, or any other "IL-4/IL-13 pathway inhibitor" as described herein) and a therapeutically effective amount of a programmed death 1 (PD-1) inhibitor (e.g., an antibody that specifically binds PD-1, PD-L1, and/or PD-L2, or any other "PD-1 inhibitor" as described herein).

In the present disclosure, references to any particular anti-IL-4R antibody and/or any particular anti-PD-1 antibody are provided to illustrate a representative IL-4/IL-13 pathway inhibitor and a representative PD-1 inhibitor, respectively, and do not limit the scope of the disclosure as combinations of other IL-4/IL-13 pathway inhibitors and PD-1 inhibitors may also be used.

As used herein, the terms "treating", "treat", or the like, mean to alleviate or reduce the severity of at least one symptom or indication, to eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, to eliminate the need for surgery, to shrink the tumor and facilitate surgery, to increase resection rate, and/or to increase duration of survival of the subject. In many embodiments, the terms "tumor", "cancer," and "malignancy" are used interchangeably and refer to one or more growths.

In some embodiments, the tumor comprises a Type 2 immunity-dependent cancer. Examples of Type 2 immunity-dependent cancers include, but are not limited to, pancreatic cancer (e.g., PDAC), breast cancer, colorectal cancer, ovarian cancer, lung cancer, lymphoma, and bladder cancer.

As used herein, the expression "a subject in need thereof" means a human or non-human mammal that exhibits one or more symptoms or indications of cancer, and/or who has been diagnosed with cancer, including a solid tumor and who needs treatment for the same. In many embodiments, the terms "subject" and "patient" are used interchangeably. The methods disclosed herein may include the step of selecting a subject in need thereof. For example, a human subject may be diagnosed with a primary or a metastatic tumor and/or with one or more symptoms or indications including, but not limited to, enlarged lymph node(s), swollen abdomen, chest pain/pressure, unexplained weight loss, fever, night sweats, persistent fatigue, loss of appetite, enlargement of spleen, itching. The expression includes subjects with primary, established, or recurrent tumor. In specific embodiments, the expression includes human subjects that have and/or need treatment for a solid tumor. In other embodiments, the expression includes human subjects that have and/or need treatment for a heme tumor (e.g., lymphomas or leukemias). The expression also includes subjects with primary or metastatic tumors (advanced malignancies). The expression also includes subjects with a tumor comprising a Type 2 immunity-dependent cancer, including but not limited to pancreatic cancer, non-small cell lung cancer, lung squamous cell carcinoma, and Hodgkin's lymphoma.

In certain embodiments, the expression includes patients with a tumor that is resistant to or refractory to or is inadequately controlled by prior therapy (e.g., treatment with an anti-cancer agent such as an IL-4/IL-13 pathway inhibitor monotherapy, a PD-1 inhibitor monotherapy, carboplatin, or docetaxel). In certain embodiments, the expression includes patients with a tumor that has been treated with one or more lines of prior therapy (e.g., surgically removed), but which has subsequently recurred. In certain embodiments, the expression includes subjects with a tumor who are not candidates for curative surgery or curative radiation, or for whom conventional anti-cancer therapy is inadvisable, for example, due to toxic side effects.

In other embodiments, the expression "a subject in need thereof" includes patients with a malignancy that has been treated but that has subsequently relapsed or metastasized. For example, patients with a tumor may have received treatment with one or more anti-cancer agents leading to tumor regression; however, subsequently have relapsed with cancer resistant to the one or more anti-cancer agents (e.g., chemotherapy-resistant cancer) may be treated with the methods of the present disclosure. In certain embodiments, the expression includes patients that exhibit upregulation of at least one cytokine, such as IL-4 and/or IL-13. In certain embodiments, the expression includes patients that exhibit increased production of at least one cytokine, such as increased production of IL-4. In certain embodiments, the expression includes patients that exhibit increased hyaluronic acid (HA) content in the tumor.

According to certain embodiments, the present disclosure includes methods for treating, delaying or inhibiting the growth of a tumor. In certain embodiments, the present disclosure includes methods to promote tumor regression. In certain embodiments, the present disclosure includes methods to reduce tumor cell load or to reduce tumor burden. In certain embodiments, the present disclosure includes methods to increase survival of the treated subject, increase response, or increase duration of response. In some embodiments, the present disclosure includes methods to treat or inhibit the growth of a tumor in subjects with pancreatic cancer, breast cancer, colorectal cancer, brain cancer, skin cancer, kidney cancer, ovarian cancer, lung cancer (e.g., non-small cell lung cancer), Hodgkin's lymphoma, or bladder cancer.

In some embodiments, the disclosed methods include administering a therapeutically effective amount of an IL-4/IL-13 pathway inhibitor and a therapeutically effective amount of a PD-1 inhibitor in combination with an additional therapeutic agent or therapy (e.g., regimen or procedure). In certain embodiments, the disclosed methods include administration of an additional therapeutic agent, such as an anti-cancer drug. As used herein, "anti-cancer drug" means any agent useful to treat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include Taxol® (paclitaxel), temozolamide, cytochalasin B, gramicidin D, ethidium bromide, emetine, cisplatin, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. The additional therapeutic agent or therapy may be administered for increasing anti-tumor efficacy, for reducing toxic effects of one or more therapies and/or for reducing the dosage of one or more therapies. In various embodiments, the additional therapeutic agent or therapy may include one or more of: chemotherapy, cyclophosphamide, surgery, radiation, a cancer vaccine, a lymphocyte activation gene 3 (LAG3) inhibitor (e.g., an anti-LAG3 antibody), a cytotoxic T-lymphocyte-associated protein 4 (CTLA-4) inhibitor (e.g., ipilimumab), a glucocorticoid-induced tumor necrosis factor receptor (GITR) agonist (e.g., an anti-GITR antibody), a T-cell immunoglobulin and mucin containing −3 (TIM3) inhibitor, a B- and T-lymphocyte attenuator (BTLA) inhibitor, a T-cell immunoreceptor with Ig and ITIM domains (TIGIT) inhibitor, a CD47 inhibitor, an indoleamine-2,3-dioxygenase (IDO) inhibitor, a vascular endothelial growth factor (VEGF) antagonist (e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)), an angiopoietin-2 (Ang2) inhibitor (e.g., nesvacumab), a transforming growth factor beta (TGFβ) inhibitor, an epidermal growth factor receptor (EGFR) inhibitor (e.g., erlotinib, cetuximab), an agonist to a co-stimulatory receptor (e.g., an agonist to CD28), a VISTA inhibitor, a CD38 inhibitor, a CD40 agonist, a CSF1R inhibitor, CCR2 inhibitor, CXCR4 inhibitor, CXCR2 inhibitor, CCR4 inhibitor, CXCL12 inhibitor, an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], an anti-CD3/anti-CD20 bispecific antibody, a vaccine (e.g., Bacillus Calmette-Guerin), granulocyte-macrophage colony-stimulating factor (GM-CSF), a cytotoxin, a chemotherapeutic agent, an IL-6R inhibitor (e.g., sarilumab), an IL-10 inhibitor, a cytokine such as IL-2, IL-7, IL-12, IL-21, and IL-15, an antibody-drug conjugate (ADC) (e.g., anti-CD19-DM4 ADC, and anti-DS6-DM4 ADC), an oncolytic virus, chimeric antigen receptor T cells (e.g., CD19-targeted T cells), an anti-inflammatory drug such as a corticosteroid, a non-steroidal anti-inflammatory drug (NSAID), and a dietary supplement such as an antioxidant.

In certain embodiments, the IL-4/IL-13 pathway inhibitor and PD-1 inhibitor may be administered in combination with therapy including a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine) and/or surgery. In certain embodiments, the IL-4/IL-13 pathway inhibitor and PD-1 inhibitor may be administered in combination with an anti-tumor therapy, including but not limited to, conventional anti-tumor therapies such as chemotherapy, radiation, surgery, or as elsewhere described herein.

In certain embodiments, the disclosed method leads to increased inhibition of tumor growth—e.g., greater tumor regression in the treated subject. For instance, the disclosed methods of administering a therapeutically effective amount of an IL-4/IL-13 pathway inhibitor and a therapeutically effective amount of a PD-1 inhibitor promotes at least about 10%, about 20%, about 30%, about 40%, about 50%, about 60%, about 70% or about 80% more tumor regression in the treated subject as compared to an untreated subject or a subject treated with either inhibitor as monotherapy.

In certain embodiments, the disclosed methods of administering a therapeutically effective amount of an IL-4/IL-13 pathway inhibitor and a therapeutically effective amount of a PD-1 inhibitor leads to delay in tumor growth and development, e.g., tumor growth may be delayed by about 3 days, more than 3 days, about 7 days, more than 7 days, more than 15 days, more than 1 month, more than 3 months, more than 6 months, more than 1 year, more than 2 years, or more than 3 years in the treated subject as compared to an untreated subject or a subject treated with either inhibitor as monotherapy.

In certain embodiments, the disclosed methods of administering a therapeutically effective amount of an IL-4/IL-13 pathway inhibitor and a therapeutically effective amount of a PD-1 inhibitor leads to complete disappearance of all evidence of tumor cells ("complete response"), leads to at least 30% or more decrease in tumor cells or tumor size ("partial response"), or leads to complete or partial disappearance of tumor cells, including new measurable tumors. Tumor reduction can be measured by any methods known in the art, e.g., X-rays, positron emission tomography (PET), computed tomography (CT), magnetic resonance imaging (MRI), cytology, histology, or molecular genetic analyses.

In certain embodiments, the disclosed methods of administering a therapeutically effective amount of an IL-4/IL-13 pathway inhibitor and a therapeutically effective amount of a PD-1 inhibitor lead to increased overall survival (OS) or progression-free survival (PFS) of the subject as compared to a subject administered with a "standard-of-care" (SOC) therapy (e.g., chemotherapy, surgery or radiation). In certain embodiments, the PFS is increased by at least one month, at least 2 months, at least 3 months, at least 4 months, at least 5 months, at least 6 months, at least 7 months, at least 8 months, at least 9 months, at least 10 months, at least 11 months, at least 1 year, at least 2 years, or at least 3 years as compared to a subject administered with any one or more SOC therapies. In certain embodiments, the OS is increased by at least one month, at least 2 months, at least 3 months, at least 4 months, at least 5 months, at least 6 months, at least 7 months, at least 8 months, at least 9 months, at least 10 months, at least 11 months, at least 1 year, at least 2 years, or at least 3 years as compared to a subject administered with any one or more SOC therapies.

In certain embodiments, the disclosed methods of administering a therapeutically effective amount of an IL-4/IL-13 pathway inhibitor and a therapeutically effective amount of a PD-1 inhibitor leads to increased response and duration of response in the treated subject, e.g., by more than 2%, more than 3%, more than 4%, more than 5%, more than 6%, more than 7%, more than 8%, more than 9%, more than 10%, more than 20%, more than 30%, more than 40% or more than 50% as compared to an untreated subject or a subject treated with either inhibitor as monotherapy.

In certain embodiments, the combination of administered inhibitors is safe and well tolerated by the subject such that there is no increase in adverse side effects as compared to a subject treated with either inhibitor as monotherapy.

In certain embodiments, the disclosed methods include administering to a subject a therapeutically effective amount of an IL-4/IL-13 pathway inhibitor and a therapeutically effective amount of a PD-1 inhibitor, wherein the subject exhibits upregulation of at least one cytokine, such as IL-4 and/or IL-13. In some embodiments, the subject exhibits greater upregulation of at least one cytokine (e.g., IL-4 and/or IL-13) as compared to a subject that is not in need of anti-tumor treatment.

In certain embodiments, the disclosed methods include administering to a subject a therapeutically effective amount of an IL-4/IL-13 pathway inhibitor and a therapeutically effective amount of a PD-1 inhibitor, wherein the subject exhibits increased production of at least one cytokine, such as increased production of IL-4. In some embodiments, the subject exhibits increased production of at least one cytokine (e.g., IL-4) as compared to a subject that is not in need of anti-tumor treatment.

In certain embodiments, the disclosed methods of administering to a subject a therapeutically effective amount of an IL-4/IL-13 pathway inhibitor and a therapeutically effective amount of a PD-1 inhibitor lead to significantly increased production of interferon gamma (IFNg) as compared to a subject treated with either inhibitor as monotherapy. In some such embodiments, these disclosed methods further lead to enhanced tumor regression and anti-tumor activity.

In certain embodiments, the disclosed methods include administering to a subject a therapeutically effective amount of an IL-4/IL-13 pathway inhibitor and a therapeutically effective amount of a PD-1 inhibitor, wherein the subject exhibits increased hyaluronic acid (HA) content in the tumor. In some such embodiments, the subject exhibits higher HA content than a subject that does not have a Type 2 immunity-dependent cancer.

In certain embodiments, the disclosed methods of administering to a subject a therapeutically effective amount of an IL-4/IL-13 pathway inhibitor and a therapeutically effective amount of a PD-1 inhibitor lead to a reduction in hyaluronic acid (HA) content in the tumor.

In certain embodiments, the disclosed methods of administering to a subject a therapeutically effective amount of an IL-4/IL-13 pathway inhibitor and a therapeutically effective amount of a PD-1 inhibitor lead to a significantly increased density of tumor-infiltrating lymphocytes (TILs), thereby enhancing cytotoxic anti-tumor efficacy of the combination therapy. In some such embodiments, these disclosed methods further lead to enhanced tumor regression and anti-tumor activity.

IL-4/IL-13 Pathway Inhibitors

The methods disclosed herein include administering a therapeutically effective amount of an IL-4/IL-13 pathway inhibitor to a subject in need thereof. As used herein, an "IL-4/IL-13 pathway inhibitor" (also referred to herein as an "IL-4/IL-13 pathway antagonist," an "IL-4/IL-13 pathway blocker," etc.) is any agent that inhibits or attenuates at least one of: (i) the binding of IL-4 and/or IL-13 to their respective receptors; (ii) signaling and/or activity of IL-4 and/or IL-13; and/or (iii) the downstream signaling/activity that results from binding of IL-4 and/or IL-13 to their respective receptors. Exemplary IL-4/IL-13 pathway inhibitors include, but are not limited to, anti-IL-4 antibodies (e.g., the antibodies disclosed in U.S. Pat. No. 7,740,843, and US Patent Application Publications 20100297110, 20160207995), anti-IL-13 antibodies (e.g., the antibodies disclosed in U.S. Pat. Nos. 7,501,121, 7,674,459, 7,807,788, 7,910,708, 7,915,388, 7,935,343, 8,088,618, 8,691,233, 9,605,065, US Patent Application Publications 20060073148, 20080044420, and EP2627673B1), bispecific antibodies that bind to IL-4 and IL-13 (e.g., the antibodies disclosed in U.S. Pat. No. 8,388,965, US Patent Application Publications 20110008345, 20130251718, 20160207995), and IL-4 receptor (IL-4R) inhibitors (described below). The portions of the publications cited herein that identify IL-4/IL-13 pathway inhibitors are hereby incorporated by reference.

In some embodiments, the IL-4/IL-13 pathway inhibitor can be an antibody, a small molecule compound, a nucleic acid, a polypeptide, or a functional fragment or variant thereof. Non-limiting examples of suitable IL-4/IL-13 pathway inhibitor antibodies include anti-IL-4 antibodies, anti-IL-13 antibodies, and anti-IL-4/IL-13 bispecific antibodies, anti-IL-4R antibodies, and antigen-binding fragments of any of the foregoing. Other non-limiting examples of suitable IL-4/IL-13 pathway inhibitors include: RNAi molecules such as anti-IL-4 RNAi molecules and anti-IL-13 RNAi, antisense molecules such as anti-IL-4 antisense RNA and anti-IL-13 antisense RNA, and dominant negative proteins such as a dominant negative IL-4 protein, a dominant negative IL-13 protein.

As used herein, an "IL-4R inhibitor" (also referred to herein as an "IL-4/IL-13 pathway inhibitor," an "IL-4Rα antagonist," an "IL-4R blocker," an "IL-4Rα blocker," etc.) is any agent which binds to or interacts with IL-4Rα or an IL-4R ligand, and inhibits or attenuates the normal biological signaling function a type 1 and/or a type 2 IL-4 receptor. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R inhibitors that can be used in the methods of the present disclosure may function by blocking IL-4-mediated signaling, IL-13-mediated signaling, or both IL-4- and IL-13-mediated signaling. The IL-4R inhibitors of the present disclosure may thus prevent the interaction of IL-4 and/or IL-13 with a type 1 or type 2 receptor.

Non-limiting examples of categories of IL-4R inhibitors include IL-4 muteins (e.g., pitrakinra), small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R inhibitors also include antigen-binding proteins that specifically bind IL-4 and/or IL-13.

Other non-limiting examples of suitable IL-4/IL-13 pathway inhibitors that can be used in the context of the present disclosure include, e.g., pitrakinra (AER-001; BAY-16-9996), aeroderm (AER-003), and the antibodies referred to and known in the art as dupilumab, pascolizumab, AMG-317, MILR1444A, CAT-354, QAX576, anrukinzumab (IMA-638), ISIS-369645 (AIR-645), IMA-026, APG-201, CNTO-607, MK-6105, MEDI9314, MED12045, tralokinumab, lebrikizumab, romilkimab, and DOM-0910.

Anti-IL-4Rα Antibodies and Antigen-Binding Fragments Thereof

According to certain exemplary embodiments of the present disclosure, the IL-4/IL-13 pathway inhibitor is an anti-IL-4Rα antibody or antigen-binding fragment thereof. The term "antibody," as used throughout the present disclosure, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the antibody (or antigen-binding portion thereof) may be identical to the human germline sequences, or may be naturally or artificially modified. An amino acid consensus sequence may be defined based on a side-by-side analysis of two or more CDRs.

The term "antibody," as used throughout the present disclosure, includes antigen-binding fragments thereof—i.e., antigen-binding fragments of full antibody molecules.

The terms "antigen-binding portion" of an antibody, "antigen-binding fragment" of an antibody, and the like, as used throughout the present disclosure, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used throughout the present disclosure.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$—$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used throughout the present disclosure, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present disclosure using routine techniques available in the art. For example, the present disclosure includes methods comprising the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, Cross-Fab, (SEED) body, leucine zipper, Duobody, IgG1/IgG2, dual acting Fab (DAF)-IgG, and Mab$^2$ bispecific formats (see, e.g., Klein et al. 2012, mAbs 4(6):653-663, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.*, 2013, 135(1):340-46).

The antibodies used in the methods of the present disclosure may be human antibodies. The term "human antibody," as used throughout the present disclosure, is intended to include antibodies having variable and constant regions derived from human germline immunoglobulin sequences. The human antibodies of the disclosure may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used throughout the present disclosure, is not intended to include antibodies in which CDR sequences derived from the germline of another mammalian species, such as a mouse, have been grafted onto human framework sequences.

The antibodies used in the methods of the present disclosure may be recombinant human antibodies. The term "recombinant human antibody," as used throughout the present disclosure, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see, e.g., Taylor et al. (1992) *Nucl. Acids Res.*, 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present disclosure specifically bind IL-4Rα. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4Rα, as used in the context of the present disclosure, includes antibodies that bind IL-4Rα or portion thereof with a $K_D$ of less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4Rα may, however, have cross-reactivity to other antigens, such as IL-4Rα molecules from other (non-human) species.

According to certain exemplary embodiments of the present disclosure, the IL-4/IL-13 pathway inhibitor is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693. In certain exemplary embodiments, the anti-IL-4Rα antibody or antigen-binding fragment thereof that can be used in the context of the methods of the present disclosure comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In yet other embodiments, the anti-IL-4R antibody or antigen-binding fragment thereof comprises an HCVR comprising SEQ ID NO: 1 and an LCVR comprising SEQ ID NO: 2. In certain embodiments, the methods of the present disclosure comprise the use of an anti-IL-4R antibody, wherein the antibody comprises a heavy chain comprising the amino acid sequence of SEQ ID NO: 9. In some embodiments, the anti-IL-4R antibody comprises a light chain comprising the amino acid sequence of SEQ ID NO: 10. An exemplary antibody comprising a HCVR comprising the amino acid sequence of SEQ ID NO: 1 and a LCVR comprising the amino acid sequence of SEQ ID NO: 2 is the fully human anti-IL-4R antibody known as dupilumab (DUPIXENT®). According to certain exemplary embodiments, the methods of the present disclosure comprise the use of dupilumab, or a bioequivalent thereof. The term "bioequivalent" with respect to dupilumab refers to anti-IL-4R antibodies or IL-4R-binding proteins or fragments thereof that are pharmaceutical equivalents or pharmaceutical alternatives having a rate and/or extent of absorption that does not show a significant difference with that of dupilumab when administered at the same molar dose under similar experimental conditions, either single dose or multiple dose. In the context of the present disclosure, the term refers to antigen-binding proteins that bind to IL-4R which do not have clinically meaningful differences with dupilumab in their safety, purity and/or potency.

According to certain embodiments of the present disclosure, the anti-human IL-4R antibody or antigen-binding fragment thereof comprises a HCVR having 90%, 95%, 98% or 99% sequence identity to SEQ ID NO: 1.

According to certain embodiments of the present disclosure, the anti-human IL-4R antibody or antigen-binding fragment thereof comprises a LCVR having 90%, 95%, 98% or 99% sequence identity to SEQ ID NO: 2.

According to certain embodiments of the present disclosure, the anti-human IL-4R antibody or antigen-binding fragment thereof comprises a HCVR comprising an amino acid sequence of SEQ ID NO: 1 having no more than 5 amino acid substitutions. According to certain embodiments of the present disclosure, the anti-human IL-4R antibody or antigen-binding fragment thereof comprises a LCVR comprising an amino acid sequence of SEQ ID NO: 2 having no more than 2 amino acid substitutions.

Sequence identity may be measured by methods known in the art (e.g., GAP, BESTFIT, and BLAST).

The present disclosure also includes use of anti-IL-4R antibodies in methods to treat cancer, wherein the anti-IL-4R antibodies comprise variants of any of the HCVR, LCVR and/or CDR amino acid sequences disclosed herein having one or more conservative amino acid substitutions. For example, the present disclosure includes use of anti-IL-4R antibodies having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein.

Other anti-IL-4Rα antibodies that can be used in the context of the methods of the present disclosure include, e.g., the antibody referred to and known in the art as AMG317 (Corren et al., 2010, *Am J Respir Crit Care Med.*, 181(8):788-796), or MEDI 9314, or any of the anti-IL-4Rα antibodies as set forth in U.S. Pat. Nos. 7,186,809, 7,605, 237, 7,638,606, 8,092,804, 8,679,487, or U.S. Pat. No. 8,877,189. The portions of the publications cited herein that identify anti-IL-4Rα antibodies are hereby incorporated by reference.

The anti-IL-4Rα antibodies used in the context of the methods of the present disclosure may have pH-dependent binding characteristics. For example, an anti-IL-4Rα antibody for use in the methods of the present disclosure may exhibit reduced binding to IL-4Rα at acidic pH as compared to neutral pH. Alternatively, an anti-IL-4Rα antibody of the present disclosure may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used throughout the present disclosure, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present disclosure if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present disclosure can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used throughout the present disclosure, the expression "acidic pH" means a pH of 6.0 or less.

PD-1 Inhibitors

The methods disclosed herein include administering a therapeutically effective amount of a PD-1 inhibitor to a subject in need thereof. As used herein, a "PD-1 inhibitor" refers to any molecule capable of inhibiting, blocking, abrogating or interfering with the activity or expression of PD-1. In some embodiments, the PD-1 inhibitor can be an antibody, a small molecule compound, a nucleic acid, a polypeptide, or a functional fragment or variant thereof. Non-limiting examples of suitable PD-1 inhibitor antibodies include anti-PD-1 antibodies and antigen-binding fragments thereof, anti-PD-L1 antibodies and antigen-binding fragments thereof, and anti-PD-L2 antibodies and antigen-binding fragments thereof. Other non-limiting examples of suitable PD-1 inhibitors include RNAi molecules such as anti-PD-1 RNAi molecules, anti-PD-L1 RNAi, and an anti-PD-L2 RNAi, antisense molecules such as anti-PD-1 antisense RNA, anti-PD-L1 antisense RNA, and anti-PD-L2 antisense RNA, and dominant negative proteins such as a dominant negative PD-1 protein, a dominant negative PD-L1 protein, and a dominant negative PD-L2 protein. Some examples of the foregoing PD-1 inhibitors are described in e.g., U.S. Pat. No. 9,308,236, U.S. Ser. No. 10/011,656, and US 20170290808, the portions of which that identify PD-1 inhibitors are hereby incorporated by reference.

Anti-PD-1 Antibodies and Antigen-Binding Fragments Thereof

In some embodiments, PD-1 inhibitors used in the methods disclosed herein are antibodies or antigen-binding fragments thereof that specifically bind PD-1.

The terms "antibody," "antigen-binding fragment," "human antibody," "recombinant antibody," and other related terminology are defined above. In the context of anti-PD-1 antibodies and antigen-binding fragments thereof, the present disclosure includes the use of bispecific antibodies wherein one arm of an immunoglobulin is specific for PD-1 or a fragment thereof, and the other arm of the immunoglobulin is specific for a second therapeutic target or is conjugated to a therapeutic moiety. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab² bispecific formats (see, e.g., Klein et al. 2012, mAbs 4(6):653-663, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.,* 2013, 135(1):340-46).

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" PD-1, as used in the context of the present disclosure, includes antibodies that bind PD-1 or a portion thereof with a $K_D$ of less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human PD-1 may, however, have cross-reactivity to other antigens, such as PD-1 molecules from other (non-human) species.

According to certain exemplary embodiments, the anti-PD-1 antibody, or antigen-binding fragment thereof comprises a heavy chain variable region (HCVR), light chain variable region (LCVR), and/or complementarity determining regions (CDRs) comprising the amino acid sequences of any of the anti-PD-1 antibodies set forth in U.S. Pat. No. 9,987,500, which is hereby incorporated by reference in its entirety. In certain exemplary embodiments, the anti-PD-1 antibody or antigen-binding fragment thereof that can be used in the context of the present disclosure comprises the heavy chain complementarity determining regions (HCDRs) of a heavy chain variable region (HCVR) comprising the amino acid sequence of SEQ ID NO: 11 and the light chain complementarity determining regions (LCDRs) of a light chain variable region (LCVR) comprising the amino acid sequence of SEQ ID NO: 12. According to certain embodiments, the anti-PD-1 antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 13; the HCDR2 comprises the amino acid sequence of SEQ ID NO: 14; the HCDR3 comprises the amino acid sequence of SEQ ID NO: 15; the LCDR1 comprises the amino acid sequence of SEQ ID NO: 16; the LCDR2 comprises the amino acid sequence of SEQ ID NO: 17; and the LCDR3 comprises the amino acid sequence of SEQ ID NO: 18. In yet other embodiments, the anti-PD-1 antibody or antigen-binding fragment thereof comprises an HCVR comprising SEQ ID NO: 11 and an LCVR comprising SEQ ID NO: 12. In certain embodiments, the methods of the present disclosure comprise the use of an anti-PD-1 antibody, wherein the antibody comprises a heavy chain comprising the amino acid sequence of SEQ ID NO: 19. In some embodiments, the anti-PD-1 antibody comprises a light chain comprising the amino acid sequence of SEQ ID NO: 20. An exemplary antibody comprising a HCVR comprising the amino acid sequence of SEQ ID NO: 11 and a LCVR comprising the amino acid sequence of SEQ ID NO: 12 is the fully human anti-PD-1 antibody known as cemiplimab (also known as REGN2810) (LIBTAYO®).

According to certain exemplary embodiments, the methods of the present disclosure comprise the use of REGN2810, or a bioequivalent thereof. As used herein, the term "bioequivalent" with respect to anti-PD-1 antibodies refers to anti-PD-1 antibodies or PD-1-binding proteins or fragments thereof that are pharmaceutical equivalents or pharmaceutical alternatives having a rate and/or extent of absorption that does not show a significant difference with that of a reference antibody (e.g., REGN2810) when administered at the same molar dose under similar experimental conditions, either single dose or multiple dose; the term "bioequivalent" also includes antigen-binding proteins that bind to PD-1 and do not have clinically meaningful differences with REGN2810 with respect to safety, purity and/or potency.

According to certain embodiments of the present disclosure, the anti-human PD-1 antibody or antigen-binding fragment thereof comprises a HCVR having 90%, 95%, 98% or 99% sequence identity to SEQ ID NO: 11.

According to certain embodiments of the present disclosure, the anti-human PD-1 antibody or antigen-binding fragment thereof comprises a LCVR having 90%, 95%, 98% or 99% sequence identity to SEQ ID NO: 12.

According to certain embodiments of the present disclosure, the anti-human PD-1 antibody or antigen-binding fragment thereof comprises a HCVR comprising an amino acid sequence of SEQ ID NO: 11 having no more than 5 amino acid substitutions. According to certain embodiments of the present disclosure, the anti-human PD-1, or antigen-binding fragment thereof, comprises a LCVR comprising an amino acid sequence of SEQ ID NO: 12 having no more than 2 amino acid substitutions.

Sequence identity may be measured by methods known in the art (e.g., GAP, BESTFIT, and BLAST).

The present disclosure also includes use of anti-PD-1 antibodies in methods to treat cancer, wherein the anti-PD-1 antibodies comprise variants of any of the HCVR, LCVR and/or CDR amino acid sequences disclosed herein having one or more conservative amino acid substitutions. For example, the present disclosure includes use of anti-PD-1 antibodies having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein.

Other anti-PD-1 antibodies that can be used in the context of the methods of the present disclosure include, e.g., the antibodies referred to and known in the art as nivolumab, pembrolizumab, MEDI0608, pidilizumab, BI 754091, spartalizumab (also known as PDR001), camrelizumab (also known as SHR-1210), sintilimab, AGEN2034, JNJ-63723283, MCLA-134, or any of the anti-PD-1 antibodies set forth in U.S. Pat. Nos. 6,808,710, 7,488,802, 8,008,449, 8,168,757, 8,354,509, 8,609,089, 8,686,119, 8,779,105, 8,900,587, and 9,987,500, and in patent publications WO2006/121168, WO2009/114335. The portions of the publications cited herein that identify anti-PD-1 antibodies are hereby incorporated by reference.

The anti-PD-1 antibodies used in the context of the methods of the present disclosure may have pH-dependent binding characteristics. For example, an anti-PD-1 antibody for use in the methods of the present disclosure may exhibit reduced binding to PD-1 at acidic pH as compared to neutral pH. Alternatively, an anti-PD-1 antibody of the present disclosure may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to PD-1 at acidic pH as compared to neutral pH" is expressed in terms of a ratio of the $K_D$ value of the antibody binding to PD-1 at acidic pH to the $K_D$ value of the antibody binding to PD-1 at neutral pH (or vice versa). For example, an antibody or antigen-binding fragment thereof may be regarded as exhibiting "reduced binding to PD-1 at acidic pH as compared to neutral pH" for purposes of the present disclosure if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present disclosure can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Anti-PD-L1 Antibodies and Antigen-Binding Fragments Thereof

In some embodiments, PD-1 inhibitors used in the methods disclosed herein are antibodies or antigen-binding fragments thereof that specifically bind PD-L1. For example, an antibody that "specifically binds" PD-L1, as used in the context of the present disclosure, includes antibodies that bind PD-L1 or a portion thereof with a $K_D$ of about $1\times10^{-8}$ M or less (e.g., a smaller $K_D$ denotes a tighter binding). A "high affinity" anti-PD-L1 antibody refers to those mAbs having a binding affinity to PD-L1, expressed as $K_D$, of at least $10^{-8}$ M, preferably $10^{-9}$ M, more preferably $10^{-10}$ M, even more preferably $10^{-11}$ M, even more preferably $10^{-12}$ M, as measured by surface plasmon resonance, e.g., BIACORE™ or solution-affinity ELISA. An isolated antibody that specifically binds human PD-L1 may, however, have cross-reactivity to other antigens, such as PD-L1 molecules from other (non-human) species.

According to certain exemplary embodiments, the anti-PD-L1 antibody, or antigen-binding fragment thereof comprises a heavy chain variable region (HCVR), light chain variable region (LCVR), and/or complementarity determining regions (CDRs) comprising the amino acid sequences of any of the anti-PD-L1 antibodies set forth in U.S. Pat. No. 9,938,345, which is hereby incorporated by reference in its entirety. In certain exemplary embodiments, an anti-PD-L1 antibody or antigen-binding fragment thereof that can be used in the context of the present disclosure comprises the heavy chain complementarity determining regions (HCDRs) of a heavy chain variable region (HCVR) and the light chain complementarity determining regions (LCDRs) of a light chain variable region (LCVR), wherein the HCVR and LCVR comprise the amino acid sequences of the anti-PD-L1 antibody designated as H1H8314N in U.S. Pat. No. 9,938,345. According to certain embodiments, the anti-PD-L1 antibody or antigen-binding fragment thereof comprises three HCDRs (HCDR1, HCDR2 and HCDR3) and three LCDRs (LCDR1, LCDR2 and LCDR3), wherein the HCDR1, HCDR2, HCDR3, LCDR1, LCDR2 and LCDR3 comprise the amino acid sequences of the anti-PD-L1 antibody designated as H1H8314N in U.S. Pat. No. 9,938,345. In yet other embodiments, the anti-PD-L1 antibody or antigen-binding fragment thereof comprises an HCVR and an LCVR that comprise the amino acid sequences of the anti-PD-L1 antibody designated as H1H8314N in U.S. Pat. No. 9,938,345.

According to certain embodiments of the present disclosure, the anti-human PD-L1, or antigen-binding fragment thereof, comprises a LCVR having 90%, 95%, 98% or 99% sequence identity to the LCVR amino acid sequence of the anti-PD-L1 antibody designated as H1H8314N in U.S. Pat. No. 9,938,345.

According to certain embodiments of the present disclosure, the anti-human PD-L1, or antigen-binding fragment thereof, comprises a HCVR comprising an amino acid sequence of the anti-PD-L1 antibody designated as H1H8314N in U.S. Pat. No. 9,938,345 having no more than 5 amino acid substitutions. According to certain embodiments of the present disclosure, the anti-human PD-L1, or antigen-binding fragment thereof, comprises a LCVR comprising an amino acid sequence of the anti-PD-L1 antibody designated as H1H8314N in U.S. Pat. No. 9,938,345 having no more than 2 amino acid substitutions.

Sequence identity may be measured by methods known in the art (e.g., GAP, BESTFIT, and BLAST).

The present disclosure also includes use of anti-PD-L1 antibodies in methods to treat cancer, wherein the anti-PD-L1 antibodies comprise variants of any of the HCVR, LCVR and/or CDR amino acid sequences disclosed herein having one or more conservative amino acid substitutions. For example, the present disclosure includes use of anti-PD-L1 antibodies having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein.

Other anti-PD-L1 antibodies that can be used in the context of the methods of the present disclosure include, e.g., the antibodies referred to and known in the art as MDX-1105, atezolizumab (TECENTRIQ™), durvalumab (IMFINZI™), avelumab (BAVENCIO™), LY3300054, FAZ053, STI-1014, CX-072, KN035 (Zhang et al., *Cell Discovery*, 3, 170004 (March 2017)), CK-301 (Gorelik et al., American Association for Cancer Research Annual Meeting (AACR), 2016-04-04 Abstract 4606), or any of the other anti-PD-L1 antibodies set forth in patent publications U.S. Pat. Nos. 7,943,743, 8,217,149, 9,402,899, 9,624,298, 9,938,345, WO 2007/005874, WO 2010/077634, WO 2013/181452, WO 2013/181634, WO 2016/149201, WO 2017/034916, or EP3177649. The portions of the publications cited herein that identify anti-PD-L1 antibodies are hereby incorporated by reference.

Pharmaceutical Compositions and Administration

The disclosed methods comprise administering an IL-4/IL-13 pathway inhibitor in combination with a PD-1 inhibitor to a subject in need thereof, wherein the inhibitors are contained within separate pharmaceutical compositions or a combined (single) pharmaceutical composition. The pharmaceutical compositions of the disclosure may be formulated with pharmaceutically acceptable carriers, excipients, and other agents that provide suitable transfer, delivery, tolerance, and the like. A multitude of appropriate formulations can be found in the formulary known to all pharmaceutical chemists: *Remington's Pharmaceutical Sciences*, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al., 1998, *J Pharm Sci Technol*, 52:238-311.

In certain embodiments, the pharmaceutical compositions of the disclosure comprise a therapeutically effective amount of an IL-4/IL-13 pathway inhibitor (such as an anti-IL-4R antibody) and/or a therapeutically effective amount of a PD-1 inhibitor (such as an anti-PD-1 antibody) and a pharmaceutically acceptable carrier. In certain embodiments, the disclosed pharmaceutical compositions are formulated for administration by injection, such as intravenous injection.

Various delivery systems are known and can be used to administer the pharmaceutical compositions of the present disclosure, e.g., encapsulation in liposomes, microparticles, microcapsules, recombinant cells capable of expressing the mutant viruses, receptor mediated endocytosis (see, e.g., Wu et al., 1987, *J. Biol. Chem.* 262: 4429-4432). Methods of administration include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, one or both pharmaceutical compositions can be delivered in a controlled release system. In one embodiment, a pump may be used. In another embodiment, polymeric materials can be used. See, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, MEDICAL APPLICATIONS OF CONTROLLED RELEASE, vol. 2, pp. 115-138). Other controlled release systems are discussed in Langer, 1990, *Science* 249:1527-1533.

Suitable injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Injectable formulations of the pharmaceutical compositions may be prepared by known methods. For example, the injectable formulation may be prepared, e.g., by dissolving, suspending or emulsifying the inhibitor (e.g., an anti-PD-1 antibody or an anti-IL-4R antibody) or a salt thereof in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injectable formulation thus prepared is preferably filled in an appropriate injection ampoule. In some embodiments, an injectable formulation may include a concentration of the inhibitor e.g., an anti-PD-1 antibody or an anti-IL-4R antibody) and one or more pharmaceutically acceptable solvents (e.g., distilled water, saline, etc.).

Exemplary pharmaceutical compositions comprising an anti-IL-4R antibody that can be used in the context of the present disclosure are disclosed, e.g., in U.S. Pat. No. 8,945,559, the portions of which that identify pharmaceutical compositions comprising an anti-IL-4R antibody are hereby incorporated by reference. Exemplary pharmaceutical compositions comprising an anti-PD-1 antibody that can be used in the context of the present disclosure are disclosed, e.g., in US 2019/0040137, the portions of which that identify pharmaceutical compositions comprising an anti-PD-1 antibody are hereby incorporated by reference.

Pharmaceutical Delivery System

In some embodiments, the pharmaceutical compositions for use in the disclosed methods may be provided in a pharmaceutical delivery system comprising: (i) a pharmaceutical composition comprising a therapeutically effective amount of an IL-4/IL-13 pathway inhibitor; and (ii) a pharmaceutical composition comprising a therapeutically effective amount of a PD-1 inhibitor. In this aspect of the disclosure, the pharmaceutical compositions are separate from each other, but may be provided in a single pharmaceutical delivery system or may be provided as a kit—i.e., a pharmaceutical delivery system with accompanying written instructions for use of the IL-4/IL-13 pathway inhibitor in combination with the PD-1 inhibitor for treating or inhibiting the growth of a tumor as disclosed herein. In certain embodiments, the pharmaceutical delivery system comprises one or more doses of the IL-4/IL-13 pathway inhibitor. In certain embodiments, the pharmaceutical delivery system comprises one or more doses of the PD-1 inhibitor.

In some embodiments, the pharmaceutical delivery system further comprises one or more additional therapeutic agents, such as any of the aforementioned additional therapeutic agents. For example, the pharmaceutical delivery system comprising a pharmaceutical composition comprising an IL-4/IL-13 pathway inhibitor and a pharmaceutical composition comprising a PD-1 inhibitor may further include one or more additional therapeutic agents selected from cyclophosphamide, a cancer vaccine, a LAG3 inhibitor (e.g., an anti-LAG3 antibody), a CTLA-4 inhibitor (e.g., ipilimumab), a GITR agonist (e.g., an anti-GITR antibody), a TIM3 inhibitor, a CD28 activator, a BTLA inhibitor, a TIGIT inhibitor, a CD38 inhibitor, a CD47 inhibitor, an IDO inhibitor, a VEGF antagonist (e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)), an Ang2 inhibitor (e.g., nesvacumab), a TGFβ inhibitor, an EGFR inhibitor (e.g., erlotinib, cetuximab), an agonist to a co-stimulatory receptor (e.g., an agonist to CD28), a VISTA inhibitor, a CD40 agonist, a CSF1R inhibitor, CCR2 inhibitor, CXCR4 inhibitor, CXCR2 inhibitor, CCR4 inhibitor, CXCL12 inhibitor, an antibody to a tumor-specific antigen [e.g., CA9, CA125, MAGE3, CEA, vimentin, tumor-M2-PK, PSA, mucin-1, MART-1, and CA19-9], an anti-CD3/anti-CD20 bispecific antibody, an oncolytic virus, a vaccine (e.g., Bacillus Calmette-Guerin), GM-CSF, a cytotoxin, a chemotherapeutic agent, an IL-6R inhibitor (e.g., sarilumab), an IL-10 inhibitor, a cytokine such as IL-2, IL-7, IL-12, IL-21, and IL-15, an ADC (e.g., anti-CD19-DM4 ADC, and anti-DS6-DM4 ADC), chimeric antigen receptor T cells (e.g., CD19-targeted T cells), an anti-inflammatory drug such as a corticosteroid, a NSAID, and a dietary supplement such as an antioxidant. In one embodiment, the pharmaceutical delivery system is used in combination with surgery in a subject in need thereof.

Administration Regimens

In some embodiments, the disclosed methods include sequentially administering a therapeutically effective amount of an IL-4/IL-13 pathway inhibitor in combination with a therapeutically effective amount of a PD-1 inhibitor to a subject in need thereof, wherein each inhibitor is administered to the subject in one or more doses, e.g., as part of a specific therapeutic dosing regimen. In certain embodiments, the methods of the present disclosure comprise administering the inhibitors for additive or synergistic activity to treat cancer, preferably a Type 2 immunity-dependent cancer, such as pancreatic cancer, breast cancer, colorectal cancer, ovarian cancer, brain cancer, skin cancer, prostate cancer, kidney cancer, lung cancer, Hodgkin's lymphoma, or bladder cancer.

As used herein, "sequentially administering" means that each dose of inhibitor is administered to the subject at a different point in time, e.g., on different days separated by a predetermined interval (e.g., hours, days, weeks or months). In some embodiments, the disclosed methods include sequentially administering to the subject a single initial dose of an IL-4/IL-13 pathway inhibitor, followed by one or more secondary doses of the IL-4/IL-13 pathway inhibitor, and optionally followed by one or more tertiary doses of the IL-4/IL-13 pathway inhibitor. In certain embodiments, the methods further comprise sequentially administering to the subject a single initial dose of a PD-1 inhibitor, followed by one or more secondary doses of the PD-1 inhibitor, and optionally followed by one or more tertiary doses of the PD-1 inhibitor.

In some embodiments, the therapeutic dosing regimen comprises administering one or more doses of an IL-4/IL-13 pathway inhibitor in combination with one or more doses of a PD-1 inhibitor. In certain embodiments, the one or more doses of an IL-4/IL-13 pathway inhibitor and/or the one or more doses of a PD-1 inhibitor are administered to the subject at a frequency of about once a day, once every two days, once every three days, once every four days, once every five days, once every six days, once a week, once every two weeks, once every three weeks, once every four weeks, once a month, once every two months, once every three months, once every four months, or less frequently.

As used herein, the expression "in combination with" means that the IL-4/IL-13 pathway inhibitor is administered before, after, or concurrent with the PD-1 inhibitor. The term "in combination with" also includes sequential or concomitant administration of an IL-4/IL-13 pathway inhibitor and a PD-1 inhibitor.

For example, when the IL-4/IL-13 pathway inhibitor is administered "before" the PD-1 inhibitor, the IL-4/IL-13 pathway inhibitor may be administered more than 150 hours, about 150 hours, about 100 hours, about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, or about 15 minutes prior to the administration of the PD-1 inhibitor. When the IL-4/IL-13 pathway inhibitor is administered "after" the PD-1 inhibitor, the IL-4/IL-13 pathway inhibitor may be administered about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, about 72 hours, or more than 72 hours after the administration of the PD-1 inhibitor. Administration of the IL-4/IL-13 pathway inhibitor "concurrent" with the PD-1 inhibitor means that the IL-4/IL-13 pathway inhibitor is administered to the subject in a separate dosage form within 15 minutes (before, after, or at the same time) of administration of the PD-1 inhibitor, or administered to the subject as a single combined dosage formulation comprising both the IL-4/IL-13 pathway inhibitor and the PD-1 inhibitor.

In certain embodiments, the disclosed methods include administration of an additional (e.g., third) therapeutic agent or therapy such as any one of the agents or therapies listed herein.

As used herein, the terms "initial," "secondary," "tertiary," and so on refer to the temporal sequence of administration. Thus, an "initial dose" is a dose that is administered at the beginning of the treatment regimen (also referred to as a "baseline dose"); a "secondary dose" is a dose administered after the initial dose; and a "tertiary dose" is a dose administered after the secondary dose. The initial, secondary, and tertiary doses may all contain the same amount of the IL-4/IL-13 pathway inhibitor or the PD-1 inhibitor. In certain embodiments, however, the amount contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an IL-4/IL-13 pathway inhibitor or PD-1 inhibitor may be administered to a patient with a cancer at a loading dose of about 1 mg/kg to about 20 mg/kg followed by one or more maintenance doses of about 0.1 mg/kg to about 10 mg/kg of the patient's body weight.

In one exemplary embodiment of the present disclosure, each secondary and/or tertiary dose is administered ½ to 14 weeks or more (e.g., ½, 1, 1½, 2, 2½, 3, 3½, 4, 5, 5½, 6, 6½, 7, 7½, 8, 8½, 9, 9½, 10, 10½ or more weeks) after the immediately preceding dose. The phrase "the immediately preceding dose," as used herein, means, in a sequence of multiple administrations, the dose of anti-PD-1 antibody administered to a subject prior to administration of the next dose in the sequence with no intervening doses.

Similarly, an "initial treatment cycle" is a treatment cycle that is administered at the beginning of the treatment regimen; a "secondary treatment cycle" is a treatment cycle administered after the initial treatment cycle; and a "tertiary treatment cycle" is a treatment cycle administered after the secondary treatment cycle. In the context of the present disclosure, treatment cycles may be the same or different from each other.

Dosage

In certain embodiments, at least one dose of the IL-4/IL-13 pathway inhibitor comprises about 0.1-50 mg/kg, such as about 0.1-10 mg/kg, of the subject's body weight. For example, at least one dose may comprise about 0.1, 1, 0.3, 3, 4, 5, 6, 7, 8, 9 or 10 mg/kg of the subject's body weight. In certain embodiments, at least one dose of the IL-4/IL-13 pathway inhibitor comprises about 0.05-1000 mg of the IL-4/IL-13 pathway inhibitor, such as about 5, 10, 15, 20, 25, 40, 45, 50, 60, 70, 80, 90, 100, 200, 300, 400, 500, 600, 700, 800, 900 mg or more of the IL-4/IL-13 pathway inhibitor. In one embodiment, the IL-4/IL-13 pathway inhibitor is REGN668 (dupilumab).

In certain embodiments, at least one dose of the PD-1 inhibitor comprises about 0.1-20 mg/kg of the subject's body weight, such as about 0.1, 1, 0.3, 3, 4, 5, 6, 7, 8, 9 or 10 mg/kg of the subject's body weight. In certain embodiments, at least one dose of the PD-1 inhibitor comprises about 0.05-500 mg of the PD-1 inhibitor, such as about 5, 10, 15, 20, 25, 40, 45, 50, 60, 70, 80, 90, 100 mg or more of the PD-1 inhibitor. In one embodiment, the PD-1 inhibitor is REGN2810 (cemiplimab).

The amounts of IL-4/IL-13 pathway inhibitor and PD-1 inhibitor administered to a subject according to the methods disclosed herein is a therapeutically effective amount. As used herein, the term "therapeutically effective amount" means an amount of each inhibitor that results in one or more of: (a) a reduction in the severity or duration of a symptom or an indication of a cancer—e.g., a tumor lesion; (b) inhibition of tumor growth, or an increase in tumor necrosis, tumor shrinkage and/or tumor disappearance; (c) delay in tumor growth and development; (d) inhibition of tumor metastasis; (e) prevention of recurrence of tumor growth; (f) increase in survival of a subject with a cancer; and/or (g) a reduction in the use or need for conventional anti-cancer therapy (e.g., elimination of need for surgery or reduced or eliminated use of chemotherapeutic or cytotoxic agents) as compared to an untreated subject or a subject treated with either inhibitor as monotherapy.

In the case of an IL-4/IL-13 pathway inhibitor (e.g., anti-IL-4R antibody), a therapeutically effective amount can be from about 0.05 mg to about 1000 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, or about 1000 mg of the IL-4/IL-13 pathway inhibitor. In certain embodiments, 10 mg, 25 mg, 50 mg, 75 mg, 150 mg, 300 mg, 600 mg, or 900 mg of an IL-4/IL-13 pathway inhibitor is administered to a subject.

In the case of a PD-1 inhibitor (e.g., an anti-PD-1 antibody), a therapeutically effective amount can be from about 0.05 mg to about 500 mg, from about 1 mg to about 500 mg, from about 10 mg to about 450 mg, from about 50 mg to about 400 mg, from about 75 mg to about 350 mg, or from about 100 mg to about 300 mg of the antibody. For example, in various embodiments, the amount of the PD-1 inhibitor is about 0.05 mg, about 0.1 mg, about 1.0 mg, about 1.5 mg, about 2.0 mg, about 5 mg, about 10 mg, about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg, of the PD-1 inhibitor.

In certain embodiments, an individual dose amount of an IL-4/IL-13 pathway inhibitor (e.g., an anti-IL-4R antibody) and/or a PD-1 inhibitor (e.g., an anti-PD-1 antibody) administered to a subject may be less than a therapeutically effective amount, i.e., a subtherapeutic dose. For example, if the therapeutically effective amount of an inhibitor comprises 3 mg/kg, a subtherapeutic dose comprises an amount less than 3 mg/kg, e.g., 2 mg/kg, 1.5 mg/kg, 1 mg/kg, 0.5 mg/kg or 0.3 mg/kg. As defined herein, a "subtherapeutic dose" refers to an amount of the inhibitor that does not lead to a therapeutic effect by itself. However, in certain embodiments, multiple subtherapeutic doses of the inhibitor may be administered to collectively achieve a therapeutic effect in the subject.

EXAMPLES

The disclosed technology is next described by means of the following examples. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the claims, along with the full scope of equivalents to which the claims are entitled. Also, while efforts have been made to ensure accuracy with respect to numbers used (e.g., amounts, temperature, etc.), some experimental errors and deviations should be accounted for. Unless indicated otherwise, parts are parts by weight, molecular weight is average molecular weight, temperature is in degrees Centigrade, and pressure is at or near atmospheric.

Example 1: In Vivo Enhanced Efficacy of an IL-4R Antibody in Combination with an Anti-PD-1 Antibody in Pancreatic Cancer Model This example relates to a study that demonstrates the enhanced anti-tumor efficacy of IL-4R blockade in monotherapy alone and in combination with anti-PD-1 therapy in vivo using the KP organoid cell subcutaneous implantation model—i.e., a mouse model of human pancreatic cancer, a Type 2 immunity-dependent cancer. In this study, 8-10 mice per treatment group were implanted with KP tumor organoid cells, and treatment of tumor-bearing mice was initiated when starting tumor volumes ranged from 30 to 110 mm³.

The IL-4/IL-13 pathway inhibitor used in this example was a mouse anti-IL-4R antibody identified as REGN1103, which is a mouse surrogate antibody of a human monoclonal antibody identified as REGN668 (also known as dupilumab) directed to human IL-4R. REGN1103 comprises a HCVR/LCVR amino acid sequence pair of SEQ ID NOs: 21/22 and has an affinity for mouse IL-4R that is in a similar range as the affinity of dupilumab for human IL-4R. In addition, REGN1103 inhibits IL-4- and IL-13-dependent proliferation of cell lines at IC50's of 1.9 nM and 11 pM, respectively.

The PD-1 inhibitor used in this example was an anti-mouse PD-1 clone identified as RPMI-14 (Bio X Cell), which is a surrogate anti-PD-1 antibody commonly used for mouse syngeneic tumor models.

Study Design

To evaluate whether a Type 2 immune response is activated in in vivo models of pancreatic cancer, IL-4 and IL-13 expression levels and IL-4 cytokine production were assessed in implantation-based models of pancreatic cancer. Balb/c mice were implanted subcutaneously or orthotopically with syngeneic tumor organoid cells engineered to express oncogenic KRAS with concomitant P53 tumor suppressor loss of function (KP), and tumors were collected 4 weeks post-implantation.

The KP organoid cells subcutaneous implantation model was also used in order to evaluate the anti-tumor efficacy of IL-4R blockade in monotherapy and/or in combination with anti-PD-1 ICB therapy in vivo.

Materials and Methods

Animals.

Balb/c mice were purchased from Jackson Laboratories, and experiments were performed according to guidelines approved by IACUC.

KP Organoid Generation.

Normal pancreatic epithelial organoids were isolated from the pancreatic tissue of a wild-type Balb/c mouse. Pancreatic tissue was minced and digested in a collagenase P buffer (Fisher Sci, 50-100-3398) at 37° C. for 15 min. Cell suspension was passed through a 500 m filter and then again through a 100 m filter. Cells were then seeded on a Matrigel overlay (VWR, 354234) with complete organoid medium; DME/F12 supplemented with 1×P/S/L-Glutamine, 1×B27 (Invitrogen), 1 mM N-Acetylcysteine (Sigma-Aldrich), 10 nM hGastrin (Sigma-Aldrich), 50 ng/ml mEGF (Life Technologies), 1 µg/ml mRSPO1 (Peprotech), 25 ng/ml hNoggin (PeproTech), 100 ng/ml hFGF10 (PeproTech), and 10 mM Nicotinamide (Sigma-Aldrich) (Boj et al., *Mol Cell Oncol*, 3(1):e1014757, 2015).

Resultant organoids were then maintained in growth factor reduced Matrigel topped with complete organoid medium supplemented with 10 nM Rock Inhibitor Y-27632 (Sigma-Aldrich, Y0503). To passage, organoids were washed out from the Matrigel using Cell Recovery Solution (Corning) for 2 hours on ice, and then dissociated into cell suspension using Accutase. Passaging was performed at 1:4 ratio once a week.

For lentivirus transduction of organoids, pancreatic organoids were dissociated into single cell suspension and transduced with lentiviruses for $KRas^{V12}$ expression and for loss of p53 expression or for expression of $p53^{R175H}$ using the spinfection method in the presence of polybrene (8 µg/ml).

Transduced KP-organoids were then implanted orthotopically into the head of the pancreas of syngeneic Balb/c mice (0.1-0.5E6 cells in 50:50 PBS/Matrigel solution per implantation), which led to tumor growth within months after implantation.

Resultant KP Tumors were collected, and pancreatic cancer cells were isolated using collagenase XI/Dispase solution overnight at 37° C. Cells were then washed in PBS and resuspended in Growth Factor Reduced Matrigel topped with complete organoid medium.

Treatments

In each treatment group (listed in Table 1 below), 8-10 mice were implanted with KP tumor organoid cells, and treatment was started once the tumors were established (30-110 mm$^3$ tumor volumes at baseline). Mice were injected intraperitoneally with 25 mg/kg of REGN1103 (anti-mIL-4R antibody) or an isotype control mIgG1 Ab in combination with 10 mg/kg of anti-mPD1 (clone RPMI-14) or isotype control rat IgG2a starting on Day 13 after KP cells injection (0.1E6 to 0.5E6 cells), every 3-4 days for 7 doses.

TABLE 1

| Group | | Administered Treatment |
|---|---|---|
| 1 | ISO/ISO | mIgG1 Ab, 25 mg/kg + rat IgG2a, 10 mg/kg |
| 2 | ILR4/ISO | Anti-IL-4R (REGN1103), 25 mg/kg + rat IgG2a, 10 mg/kg |
| 3 | ISO/PD-1 | mIgG1 Ab, 25 mg/kg + Anti-PD-1 (RPMI-14, BioXCell), 10 mg/kg |
| 4 | IL4R/PD-1 | Anti-IL-4R (REGN1103), 25 mg/kg + Anti-PD-1 (RPMI-14, BioXCell), 10 mg/kg |

Balb/c mice received 1 E5-2.5E5 syngeneic KP organoid-derived cells subcutaneously in a 50:50 PBS/Matrigel solution. Cells were tested using the IMPACT test before in vivo implantations. Tumors were measured twice weekly by calipers, and the volume was calculated by $(L*W^2)/2$, where L is the longest diameter and W is the perpendicular diameter.

Results

IL-4 and IL-13 gene expression were found to be massively upregulated in the orthotopically and subcutaneously implanted tumors relative to normal pancreas, which lacked expression of IL-4 and IL-13 genes. Similarly, IL-4 cytokine production, as measured by ELISA assay, was massively upregulated in both the orthotopic and subcutaneous tumor models, whereas normal pancreas showed no production of IL-4 cytokine. These data show that KP organoid cells-implantation tumor models of pancreatic cancer express high levels of IL-4 and IL-13, which are the two central Type 2-associated cytokines, thereby showing that Type 2 immune response is activated in these in vivo models of pancreatic cancer.

Figure 1B:
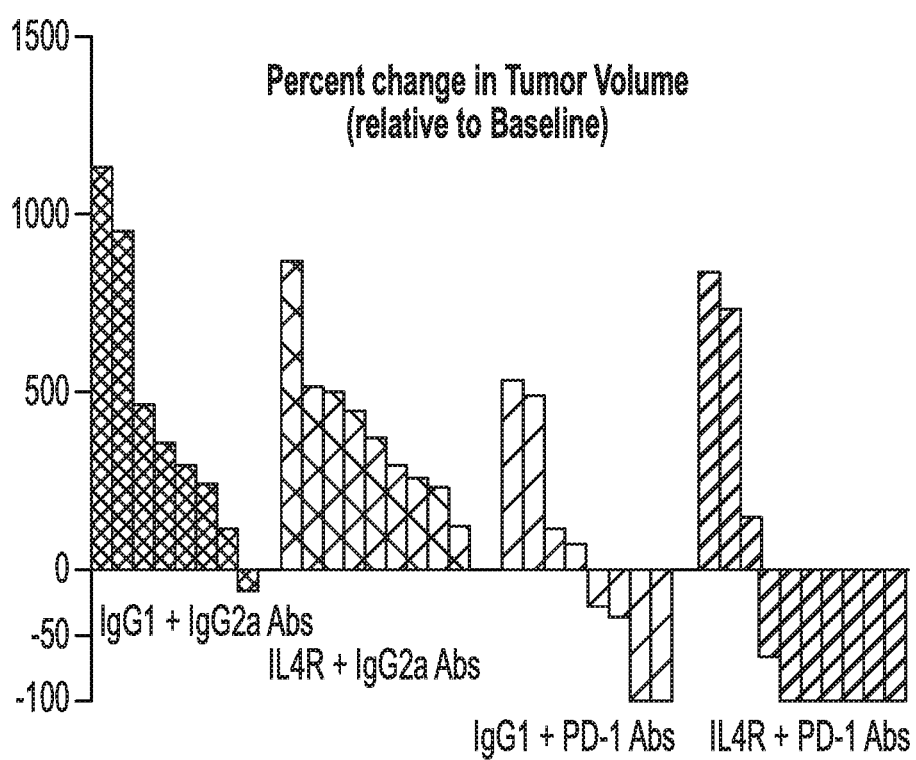
FIG. 1B is a bar graph showing percent change in tumor volume in individual animals, from 30-110 mm$^3$ tumor volumes at baseline to Day 38, in accordance with the study described in Example 1.
Figure 2A:
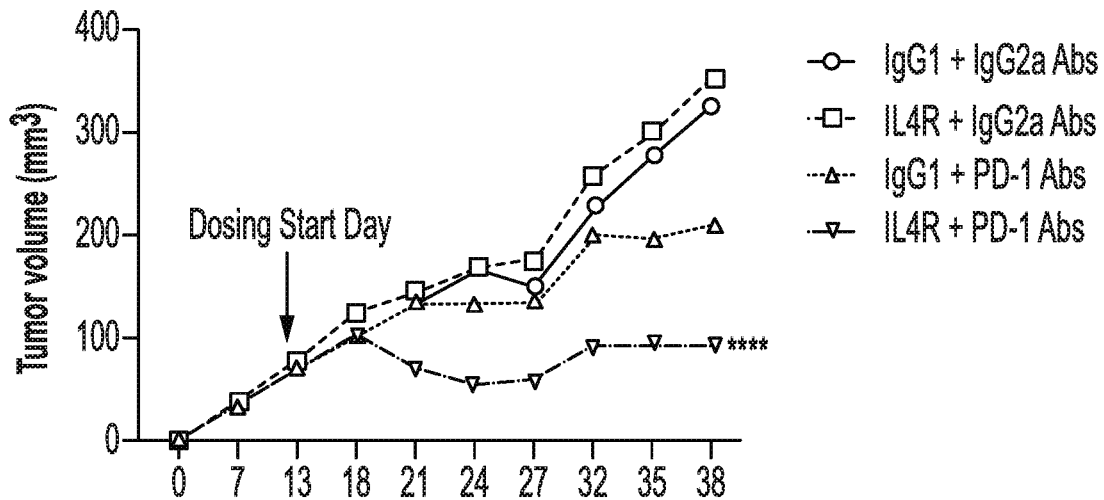
FIG. 2A is a line graph showing tumor volume reduction from 50-110 mm$^3$ tumor volumes at baseline in accordance with the repeated study described in Example 1. The asterisks (*) indicate degree of statistical significance relative to isotype controls (IgGs).
Figure 2B:
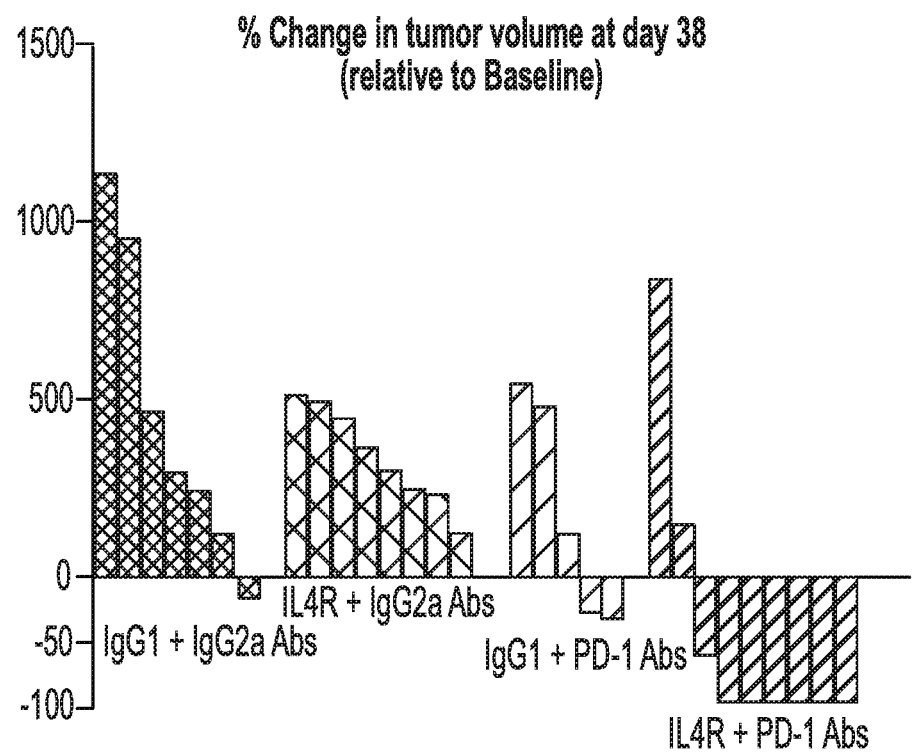
FIG. 2B is a bar graph showing percent change in tumor volume in individual animals, from 50-110 mm$^3$ tumor volumes at baseline to Day 38, in accordance with the repeated study described in Example 1.

Further, anti-IL-4R treatment enhanced the anti-tumor efficacy of PD-1 blockade in vivo. Results of the treatment study with 30-110 mm$^3$ tumor volumes at baseline are illustrated in FIGS. 1A and 1B. Results of a sub-group of treated mice with tumors of 50-110 mm$^3$ tumor volume at baseline are illustrated in FIGS. 2A and 2B. Anti-mPD-1 monotherapy showed partial anti-tumor efficacy with 4 out of 8 mice showing tumor regression, including 2 complete responses, while anti-mIL-4R monotherapy showed no anti-tumor activity. However, the combination therapy of anti-IL-4R and anti-PD-1 showed dramatically enhanced anti-tumor efficacy with 7 out of 10 mice exhibiting tumor regression, including 6 complete regressions. This was an unexpectedly superior result.

Thus, IL-4/IL-13 Type 2 immune responses in Type 2 immunity-dependent cancers can be effectively targeted by blockade of the IL-4/IL-13 pathway. This study shows that anti-IL-4R therapy substantially enhances the anti-tumor efficacy of anti-PD-1 treatment to a surprising degree in a subcutaneous animal model of pancreatic cancer, which is representative of Type 2 immunity-dependent cancers.

Example 2: Human Pancreatic Cancer and Subsets in Other Human Cancer Types Show Strong Type 2 Immune Signature To assess the extent of Type 2 immune response activation within and across human cancer types, a Type 2 immune gene signature was designed, which includes Type 2-associated cytokines, chemokines, and their receptors, as well as Type 2 immunity downstream target genes (IL-13RA2, IL25, IL17RB, SERPINB2, CCL24, CEACAM1, CCL1, MUC5B, CCL26, IL-13RA1, POSTN, IL6R, CCL18, CCL17, FCER2, CCR3, IL6, CCL8, CRLF2, IL33, TSLP, IL-4R, CCR4, PTGDR, FCER1A, IL1RL1, DPP4, IL-4, IL5, and IL-13). This Type 2 immune signature was applied to the expression profiles of multiple human cancer types available from The Cancer Genome Atlas (TCGA) database—namely, BRCA (breast cancer), COAD (colon adenocarcinoma), GBM (glioblastoma multiforme), KIRC (kidney renal cell carcinoma), LGG (low grade glioma), LUAD (lung adenocarcinoma), LUSC (lung squamous cell carcinoma), OV (ovarian cancer), PAAD (pancreatic adenocarcinoma), PRAD (prostate adenocarcinoma), and SKCM (skin cutaneous melanoma). The upper quantile normalized expression values in FPKM (Fragments per Kilobase of transcript per Million mapped reads) were used as original input. Z-Scores were generated for each gene expression across all tumor samples presented in the heatmap. For the Th2 signature score calculation, the ceiling of Z-Score (the highest Z-Score) was set +4; and the floor of Z-Score (the lowest Z-Score) was set at −4. Then the sum of Z-Scores for each of the genes in the Th2 signature gene list was computed for each sample. The combined expression (Z-Score) represents the sample's Th2 signature level.

Analysis of this Type 2 immune signature heatmap showed that pancreatic cancer, non-small cell lung cancer, and lung squamous cell carcinoma display the strongest overall expression of this Type 2 immune signature with minimal heterogeneity. Subsets within other cancer types showed a strong overall Type 2 immune signature as well, including subsets in breast and colon cancer. However, other cancer types (e.g., glioblastoma multiforme (GBM), glioma, melanoma, prostate) displayed overall low expression of the signature. In summary, these data indicate strong Type 2 immune activity in human pancreatic and lung cancers, as well as in subsets of other human cancer types, including breast and colon cancers.

Example 3: IL-4 and IL-13 Cytokines are Massively Upregulated and Produced in a Pancreatic Cancer In Vivo Model This example relates to a study of whether a Type 2 immune response is activated in in vivo models of pancreatic cancer, by assessing IL-4 and IL-13 expression levels and IL-4 cytokine production in implantation based-models of pancreatic cancer. The Materials and Methods described in Example 1 regarding Animals and KP Organoid Generation are the same for this Example 3.

Balb/c mice were implanted subcutaneously (Sub-Cu) or orthotopically (Ortho) with syngeneic pancreatic tumor organoid cells engineered to express oncogenic KRAS with concomitant P53 tumor suppressor loss of function (KP cells), and tumors were collected 4 weeks post-implantation (n=4-5 mice per condition).

Cytokine Measurements.

Tumor samples were resuspended in tissue protein extraction reagent (T-PER; Thermo Fisher, Waltham, Mass.)

supplemented with a protease inhibitor cocktail and mechanically homogenized with a TissueLyser II (Qiagen, Hilden, Germany). Total protein content in tumor protein extracts was measured by using a Bradford assay (Pierce™ 660 nm Protein Assay (Thermo Fisher, Waltham, Mass.). Cytokine concentrations were determined by using custom MSD kits and a QuickPlex SQ120 plate reader (Meso Scale Discovery, Rockville, MD).

Results

Figure 3B:
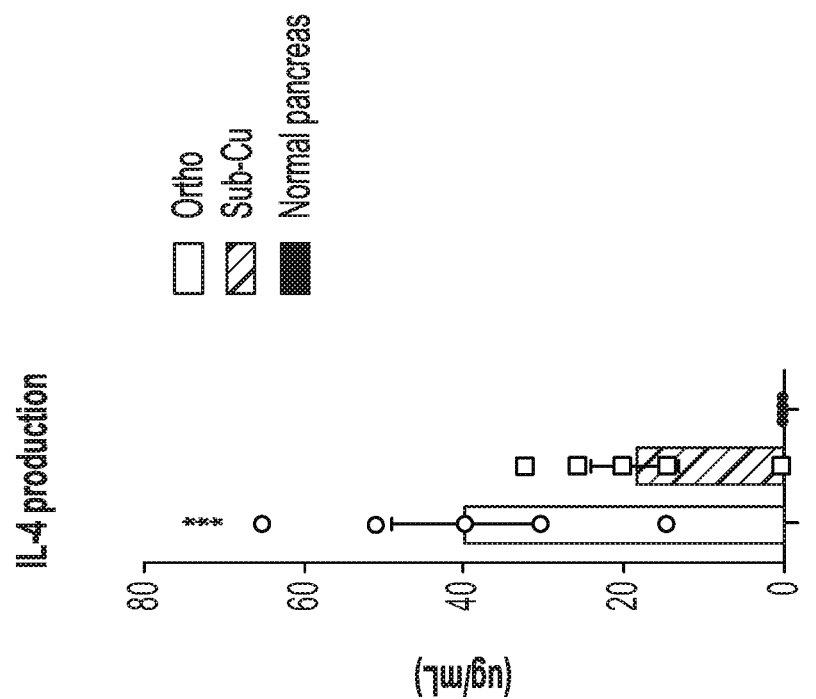
FIG. 3B is a bar graph showing IL-4 cytokine production in Balb/c mice implanted subcutaneously (Sub-Cu) or orthotopically (Ortho) with syngeneic pancreatic tumor organoid cells engineered to express oncogenic KRAS with concomitant P53 tumor suppressor loss of function (KP cells), as described in Example 3.
Figure 3A:
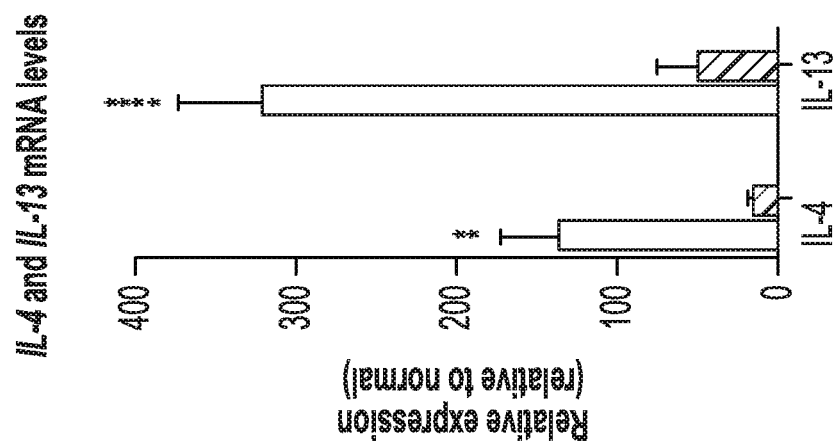
FIG. 3A is a bar graph showing expression of IL-4 and IL-13 mRNA relative to normal in Balb/c mice implanted subcutaneously (Sub-Cu) or orthotopically (Ortho) with syngeneic pancreatic tumor organoid cells engineered to express oncogenic KRAS with concomitant P53 tumor suppressor loss of function (KP cells), as described in Example 3.

Both IL-4 and IL-13 gene expression was found to be massively upregulated in the orthotopically and subcutaneously implanted-tumors relative to normal pancreas, which lacked expression of IL-4 and IL-13 genes (FIG. 3A). Similarly, IL-4 cytokine production, as measured by ELISA assay was massively upregulated in both the orthotopic and subcutaneous tumor models, whereas normal pancreas showed no production of IL-4 cytokine (FIG. 3B). These data show that KP organoid cell-implantation tumor models of pancreatic cancer express high levels of IL-4 and IL-13, the two central Type 2 immunity-associated cytokines, thereby showing that Type 2 immune response is activated in these in vivo models of pancreatic cancer. Thus, IL-4/IL-13-induced Type 2 immune responses can be effectively targeted via IL-4R blockade (Harb et al., *Clin Exp Allergy*, 50(1):5-14, 2019; Le Floc'h et al., *Allergy*, December 2019).

Example 4: Combined Anti-IL-4R and Anti-PD-1 Blockade Consistently Results in Enhanced Anti-Tumor Efficacy In Vivo in Larger Tumors This example is a repeat study of Example 1 and assessed the efficacy of combined anti-IL-4R/PD-1 combination therapy on larger tumors. Specifically, in this study, treatment was started when established tumors had a volume in the range of 70 to 100 mm$^3$.

Results

Figure 4A:
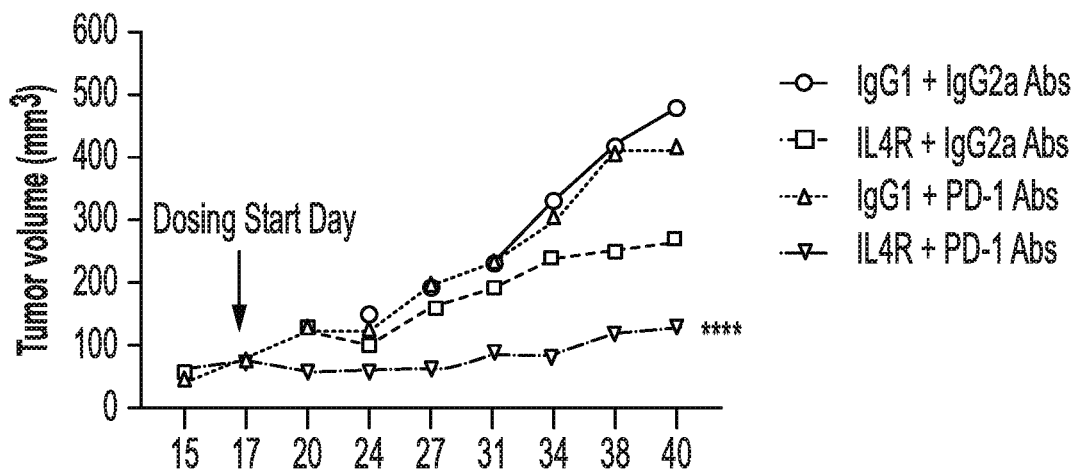
FIG. 4A is a line graph showing tumor volume reduction from 70-100 mm$^3$ tumor volumes at baseline to Day 40, in accordance with the study described in Example 4. The asterisks (*) indicate degree of statistical significance relative to isotype controls (IgGs).
Figure 4B:
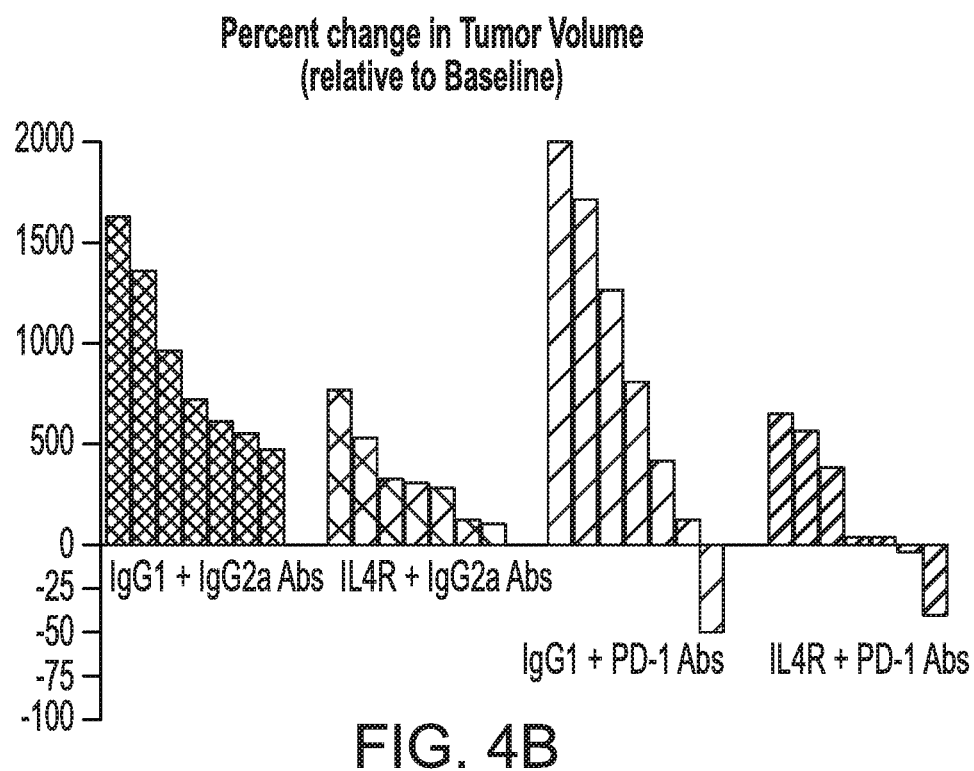
FIG. 4B is a bar graph showing percent change in tumor volume in individual animals, from 70-100 mm$^3$ tumor volumes at baseline to Day 40, in accordance with the study described in Example 4.

Anti-IL4R monotherapy showed a trend towards tumor growth control, while anti-mPD-1 monotherapy showed no overall anti-tumor activity. In contrast, anti-IL-4R/PD-1 combination therapy showed significantly enhanced anti-tumor efficacy relative to monotherapy control arms, controlling tumor growth in 4 out of 7 mice. Results of this treatment study are illustrated in FIGS. 4A and 4B.

Figure 4C:
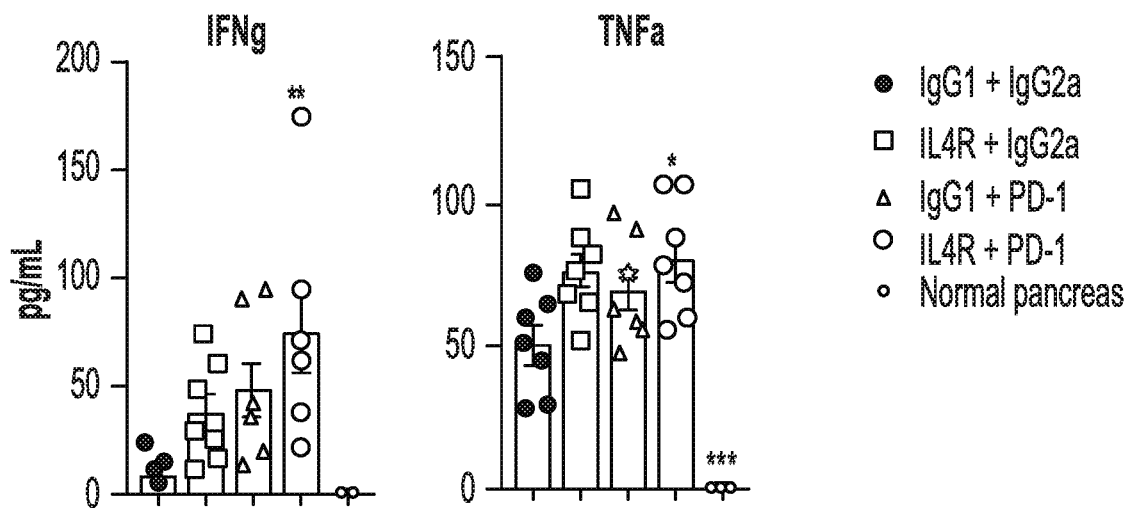
FIG. 4C is a pair of bar graphs showing systemic interferon gamma (IFNg) and tumor necrosis factor alpha (TNFa) cytokine levels measured in tumor lysates at the end of the study described in Example 4.

Additionally, systemic interferon gamma (IFNg) and tumor necrosis factor alpha (TNFa) cytokine levels were measured in tumor lysates at the end-of-study time point. IFNg and TNFa production were significantly increased in the combination treatment group compared to single agent or isotype control groups (FIG. 4C). In particular, the highest levels of intra-tumoral IFNg (>50 pg/mL) corresponded to the most responsive tumors in each treatment group. Overall, the foregoing findings indicate that anti-IL-4R/PD-1 combination therapy induced increased IFNg dependent anti-tumor activity.

Figure 5A:
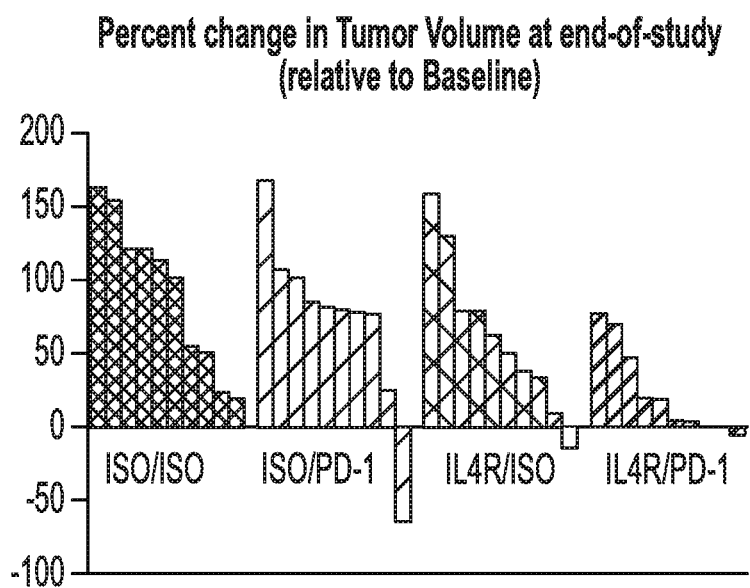
FIG. 5A is a bar graph showing percent change in tumor volume in individual animals, from 50-100 mm$^3$ tumor volumes at baseline to end-of-study, in accordance with the study described in Example 5.

Example 5: Combined Anti-IL-4R and Anti-PD-1 Blockade Shows Tumor Stroma and Tumor Immune Modulating Activities This example is a repeat study of Example 1 but investigated the stroma and immune modulating activities of anti-IL-4R/PD-1 combination therapy in PDAC tumor-bearing mice. Histological analysis of stromal content was performed in this short-end point treatment study, in which 8-10 mice per treatment group were implanted with KP tumor organoid cells. Treatment was started when tumor volumes reached 50-100 mm$^3$. Tumors were collected after 2 treatment doses to avoid excessive tumor regression, allowing unbiased histological analysis. The percent change in tumor volume of the treatment groups is shown in FIG. 5A.

Figure 5C:
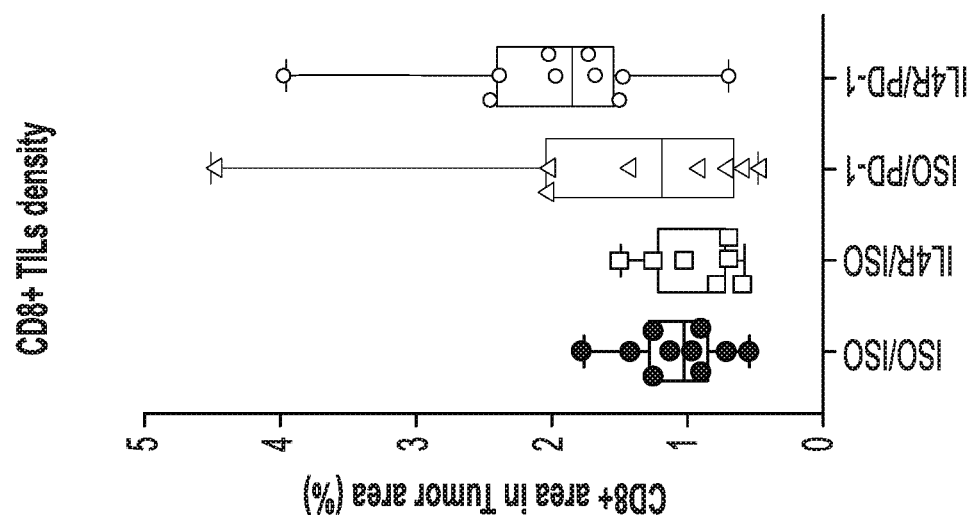
FIG. 5C is a bar graph showing CD8+ T cells infiltration within the tumor bed as represented by histological quantification of the tumor-infiltrating lymphocyte (TIL) marker CD8 for four treatment groups: ISO/ISO, IL-4R/ISO, ISO/PD-1, and IL-4R/PD-1, in accordance with the study described in Example 5.
Figure 5B:
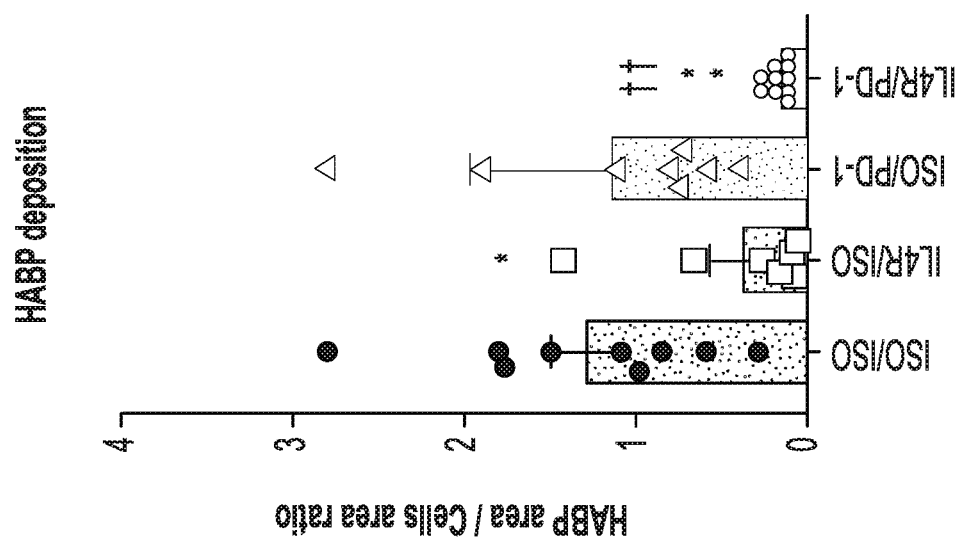
FIG. 5B is a bar graph showing hyaluronic acid (HA) content in pancreatic tumors as represented by a histochemical staining method using biotinylated HA-binding protein (HABP) for four treatment groups: ISO/ISO, IL-4R/ISO, ISO/PD-1, and IL-4R/PD-1, in accordance with the study described in Example 5.

Hyaluronic Acid (HA) is a prominent component of the pancreatic tumor microenvironment that has been shown to inhibit drug perfusion within the tumor bed (Provenzano et al., *Cancer Cell*, 21(3):418-29, 2012, Jacobetz et al., *Gut*, 62(1):112-20, 2013). Enzymatic depletion of HA has been shown to enhance cytotoxic anti-tumor efficacy in PDAC preclinical models and is investigated in pancreatic cancer patients in combination with chemotherapy or immune checkpoint blockade. HA content in the microenvironment of pancreatic tumors was determined using a histochemical staining method using biotinylated HA-binding protein (HABP) and digital pathology analysis (FIG. 5B).

Immunostaining.

Samples were fixed in 10% neutral formalin for 16-24 h and transferred in 70% ethanol for paraffin embedding. All stainings were performed on 5 uM paraffin sections of mouse tissue.

For immunostaining, sections were deparaffinized, rehydrated and antigen retrieval was performed with RTU AR Citra Solution (Biogenex, San Ramon, CA). H$_2$O$_2$ was used to block endogenous peroxidases. Non-specific protein binding was blocked with 10% goat serum (Sigma, St Louis, MA). Sections were incubated with anti-CD8 primary antibody (Cell Signaling Technologies, Danvers, MA) overnight at 4° C. and horseradish peroxidase conjugated secondary antibody (Cell Signaling Technologies). Remaining steps were carried out using appropriate Vectastain Elite ABC kits (Vector Labs.) and DAB Peroxidase Substrate (Vector Labs., with haematoxylin counterstaining. Digital Quantification for HABP deposition and CD8 T cell density were performed using the HALO image analysis platform from Indica Labs.

Ha Histochemistry.

Biotinylated HA binding protein (bHABP, Millipore Danvers MA USA was used. Sections were deparaffinized, rehydrated and blocked with 3% bovine serum albumin (BSA) prior to incubation with bHABP (1:200 in 1% BSA) overnight at 4° C. Remaining steps were carried out using Vectastain Elite ABC kit Standard (Vector Labs. Burlingame CA) and DAB Peroxidase Substrate (Vector Labs.), with haematoxylin counterstaining.

Results

FIG. 5A shows the percent change in tumor volume (relative to baseline) at the end of the study. HA content was dramatically reduced in the anti-IL-4R monotherapy group and in the anti-IL-4R/PD-1 combination therapy group as compared to the anti-PD-1 monotherapy and isotype control groups (FIG. 5B). This reduction of HA content was associated with an increase in CD8+ T cells infiltration within the tumor bed in the anti-IL-4R/PD-1 combination therapy group specifically, as shown by the histological quantification of the tumor-infiltrating lymphocyte (TIL) marker CD8 (FIG. 5C). Additionally, increased T cell infiltration was associated with a marked synergistic anti-tumor efficacy in the anti-IL-4R/PD-1 combination therapy group.

The foregoing data show that in the context of type 2 immune-polarized fibrotic pancreatic tumors, IL-4R blockade exerts anti-tumor activity via a two-fold mechanism of action: (i) potent stromal modulation and regulation of HA deposition; and (ii) significant enhancement of TIL infiltration when combined with anti-PD-1 therapeutics.

Example 6: Efficacy of Anti-Human PD-1 Antibody in Combination with Anti-IL-4R Antibody Against Implanted Tumors For the experiments in this Example, humanized mice that express the extracellular portion of human PD-1 and the transmembrane and intracellular portions of the mouse version of the protein were generated using VelociGene® technology (Valenzuela et al 2003, *Nat. Biotechnol.* 21:652-659; see also U.S. Pat. No. 9,987,500).

The exemplary anti-PD-1 antibody used for this study is a fully human antibody (cemiplimab) that binds specifically to human PD-1 and comprises HCDR1-HCDR2-HCDR3-LCDR1-LCDR2-LCDR3 of SEQ ID NOs: 13-14-15-16-17-18 and HCVR/LCVR of SEQ ID NOs: 11/12. The exemplary IL-4/IL-13 pathway inhibitor used in this example is described in Example 1.

Pancreatic epithelial organoids are isolated from a PD-1 humanized mouse and processed as described in Example 1 to yield KP-tumor organoid cells (pancreatic cancer cells).

PD-1-humanized mice are implanted with $1.5 \times 10^6$ KP-tumor organoid cells on day 0 and treatment is started once the tumors are established. Mice are injected intraperitoneally with 25 mg/kg of REGN1103 (anti-mIL-4R antibody) or an isotype control Ab in combination with 10 mg/kg of cemiplimab or isotype control starting on Day 13 after KP cells injection (0.1 E6 to 0.5E6 cells), every 3-4 days for 7 doses. Tumor volumes are monitored by caliper measurement twice per week for the duration of the experiment.

Anti-IL-4R treatment enhances the anti-tumor efficacy of cemiplimab. Tumor regression and complete responses are seen in mice treated with the combination therapy as compared to Cemiplimab Monotherapy.

Example 7: Clinical Study

In a clinical study, patients with pancreatic cancer, lung cancer, multiple myeloma, breast cancer and colon cancer are administered cemiplimab in combination with dupilumab. Patients that are administered cemiplimab and dupilumab show greater tumor inhibition than patients that are administered either drug as monotherapy.

We claim:

1. A method of treating or inhibiting the growth of a tumor, comprising:
   (a) selecting a subject with a Type 2 immunity-dependent cancer; and
   (b) administering to the subject a therapeutically effective amount of an anti-interleukin-4 receptor (IL-4R) antibody and a therapeutically effective amount of an anti-programmed death 1 (PD-1) antibody;
   wherein:
   the anti-IL-4R antibody comprises a heavy chain variable region (HCVR) comprising the amino acid sequence of SEQ ID NO: 1 and a light chain variable region (LCVR) comprising the amino acid sequence of SEQ ID NO: 2; and
   the anti-PD-1 antibody comprises a HCVR comprising three heavy chain complementarity determining regions (CDRs) (HCDR1, HCDR2 and HCDR3) and a LCVR comprising three light chain CDRs (LCDR1, LCDR2 and LCDR3), wherein: HCDR1 has the amino acid sequence of SEQ ID NO: 13; HCDR2 has the amino acid sequence of SEQ ID NO: 14; HCDR3 has the amino acid sequence of SEQ ID NO: 15; LCDR1 has the amino acid sequence of SEQ ID NO: 16; LCDR2 has the amino acid sequence of SEQ ID NO: 17; and LCDR3 has the amino acid sequence of SEQ ID NO: 18.

2. The method according to claim 1, wherein the Type 2 immunity-dependent cancer is pancreatic cancer, breast cancer, colorectal cancer, ovarian cancer, brain cancer, skin cancer, prostate cancer, kidney cancer, lung cancer, Hodgkin's lymphoma, or bladder cancer.

3. The method according to claim 1, wherein the Type 2 immunity-dependent cancer is pancreatic cancer.

4. The method according to claim 1, wherein the Type 2 immunity-dependent cancer is non-small cell lung cancer.

5. The method according to claim 1, wherein the Type 2 immunity-dependent cancer is lung squamous cell carcinoma.

6. The method according to claim 1, wherein the cancer is primary, metastatic, or recurrent.

7. The method according to claim 1, wherein the subject has been treated with a prior anti-tumor therapeutic agent or therapy.

8. The method according to claim 1, wherein the subject has been treated with a PD-1 inhibitor.

9. The method according to claim 1, wherein the cancer is resistant or non-responsive to prior treatment with a therapeutic agent or therapy.

10. The method according to claim 1, wherein the subject exhibits upregulation of at least one cytokine.

11. The method according to claim 10, wherein the at least one cytokine comprises at least one of IL-4 and IL-13.

12. The method according to claim 1, wherein the subject exhibits increased production of at least one cytokine.

13. The method according to claim 12, wherein the at least one cytokine comprises IL-4.

14. The method according to claim 1, wherein the subject exhibits increased hyaluronic acid (HA) content in the tumor.

15. The method according to claim 1, wherein the HCVR of the anti-IL-4R antibody comprises three heavy chain CDRs (HCDR1, HCDR2 and HCDR3) and the LCVR of the anti-IL-4R antibody comprises three light chain CDRs (LCDR1, LCDR2 and LCDR3), wherein: HCDR1 has the amino acid sequence of SEQ ID NO: 3; HCDR2 has the amino acid sequence of SEQ ID NO: 4; HCDR3 has the amino acid sequence of SEQ ID NO: 5; LCDR1 has the amino acid sequence of SEQ ID NO: 6; LCDR2 has the -amino acid sequence of SEQ ID NO: 7; and LCDR3 has the amino acid sequence of SEQ ID NO: 8.

16. The method according to claim 1, wherein the anti-IL-4R antibody comprises a heavy chain and a light chain, wherein the heavy chain has the amino acid sequence of SEQ ID NO: 9.

17. The method according to claim 1, wherein the anti-IL-4R antibody comprises a heavy chain and a light chain, wherein the light chain has the amino acid sequence of SEQ ID NO: 10.

18. The method according to claim 1, wherein the anti-IL-4R antibody comprises a heavy chain and a light chain, wherein the heavy chain has the amino acid sequence of SEQ ID NO: 9 and the light chain has the amino acid sequence of SEQ ID NO: 10.

19. The method according to claim 1, wherein the anti-IL-4R antibody is dupilumab or a bioequivalent thereof.

20. The method according to claim 1, wherein the HCVR of the anti-PD-1 antibody comprises the amino acid sequence of SEQ ID NO: 11 and the LCVR of the anti-PD-1 antibody comprises the amino acid sequence of SEQ ID NO: 12.

21. The method according to claim 1, wherein the anti-PD-1 antibody comprises a heavy chain and a light chain, wherein the heavy chain has the amino acid sequence of SEQ ID NO: 19.

22. The method according to claim 1, wherein the anti-PD-1 antibody comprises a heavy chain and a light chain, wherein the light chain has the amino acid sequence of SEQ ID NO: 20.

23. The method according to claim 1, wherein the anti-PD-1 antibody comprises a heavy chain and a light chain, wherein the heavy chain has the amino acid sequence of SEQ ID NO: 19 and the light chain has the amino acid sequence of SEQ ID NO: 20.

24. The method according to claim 1, wherein the anti-PD-1 antibody is cemiplimab or a bioequivalent thereof.

25. The method according to claim 1, wherein the anti-PD-1 antibody is cemiplimab.

26. The method according to claim 1, wherein one or more doses of the anti-IL-4R antibody is administered in combination with one or more doses of the anti-PD-1 antibody.

27. The method according to claim 26, wherein at least one dose of the anti-IL-4R antibody comprises about 0.1 mg/kg to about 50 mg/kg of the subject's body weight.

28. The method according to claim 26, wherein at least one dose of the anti-IL-4R antibody comprises about 0.05 to about 1000 mg.

29. The method according to claim 26, wherein each dose of the anti-IL-4R antibody is administered 0.5 to 12 weeks after the immediately preceding dose.

30. The method according to claim 26, wherein at least one dose of the anti-PD-1 antibody comprises about 0.1 mg/kg to about 20 mg/kg of the subject's body weight.

31. The method according to claim 26, wherein at least one dose of the anti-PD-1 antibody comprises about 0.05 to about 500 mg.

32. The method according to claim 26, wherein each dose of the anti-PD-1 antibody is administered 0.5 to 12 weeks after the immediately preceding dose.

33. The method according to claim 1, wherein the anti-IL-4R antibody is administered concurrently with the anti-PD-1 antibody.

34. The method according to claim 1, wherein the anti-IL-4R antibody is administered prior to the anti-PD-1 antibody.

35. The method according to claim 1, wherein the anti-IL-4R antibody is administered after the anti-PD-1 antibody.

36. The method according to claim 1, wherein the method promotes tumor regression, delays tumor growth, reduces tumor cell load, reduces tumor burden, and/or prevents tumor recurrence in the subject.

37. The method according to claim 1, wherein the method promotes at least about 10% more tumor regression in the treated subject as compared to an untreated subject or a subject treated with either antibody as monotherapy.

38. The method according to claim 1, wherein the method leads to at least 30% or more decrease in tumor cells or tumor size as compared to an untreated subject or a subject treated with either antibody as monotherapy.

39. The method according to claim 1, further comprising administering at least one additional therapeutic agent or therapy.

40. The method according to claim 39, wherein the additional therapeutic agent or therapy comprises chemotherapy, cyclophosphamide, surgery, radiation, a cancer vaccine, a Lymphocyte Activation Gene 3 (LAG3) inhibitor, a Glucocorticoid-Induced TNFR-Related (GITR) agonist, a T-cell immunoglobulin and mucin domain 3 (TIM3) inhibitor, a B- and T-lymphocyte attenuator (BTLA) inhibitor, a T-cell immunoreceptor with immunoglobulin and immunoreceptor tyrosine-based inhibition motif domain (TIGIT) inhibitor, a Cluster of Differentiation 38 (CD 38) inhibitor, a Cluster of Differentiation 47 (CD47) inhibitor, an Indoleamine 2, 3-dioxygenase 1 (IDO1) inhibitor, an Indoleamine 2, 3-dioxygenase 2 (IDO2) inhibitor, a Vascular Endothelial Growth Factor (VEGF) antagonist, an Angiopoietin 2 (Ang2) inhibitor, a Transforming Growth Factor Beta (TGFB) inhibitor, an Epidermal Growth Factor Receptor (EGFR) inhibitor, a V-domain Ig suppressor of T cell activation (VISTA) inhibitor, a Cluster of Differentiation 40 (CD40) agonist, a Colony Stimulating Factor 1 Receptor (CSF1R) inhibitor, C-C Motif Chemokine Receptor 2 (CCR2) inhibitor, C-X-C Motif Chemokine Receptor 4 (CXCR4) inhibitor, C-X-C Motif Chemokine Receptor 2 (CXCR2) inhibitor, C-C Motif Chemokine Receptor 4 (CCR4) inhibitor, C-X-C Motif Chemokine Ligand 12 (CXCL12) inhibitor, a Cluster of Differentiation 28 (CD28) activator, an agonist to a co-stimulatory receptor, an antibody to a tumor-specific antigen, an anti-Cluster of Differentiation 3 (CD3)/anti-Cluster of Differentiation 20 (CD20) bispecific antibody, Granulocyte-Macrophage Colony-Stimulating Factor (GM-CSF), a cytotoxin, an oncolytic virus, an Interleukin 6 Receptor (IL-6R) inhibitor, an Interleukin 10 Receptor (IL-10) inhibitor, a cytokine, an antibody-drug conjugate (ADC), chimeric antigen receptor T cells, an anti-inflammatory drug, a non-steroidal anti-inflammatory drug (NSAID), and/or a dietary supplement.

* * * * *

SEQUENCE LISTING

```
<160> NUMBER OF SEQ ID NOS: 22

<210> SEQ ID NO 1
<211> LENGTH: 124
<212> TYPE: PRT
<213> ORGANISM: Artificial Sequence
<220> FEATURE:
<223> OTHER INFORMATION: R668 HCVR

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: R668 LCVR

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30
```

```
Ile Gly Tyr Asn Tyr Leu Asp Trp Tyr Leu Gln Lys Ser Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 3
<211> LENGTH: 8
<212> TYPE: PRT
<213> ORGANISM: Artificial Sequence
<220> FEATURE:
<223> OTHER INFORMATION: R668 HCDR1

<400> SEQUENCE: 3

Gly Phe Thr Phe Arg Asp Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: R668 HCDR2

<400> SEQUENCE: 4

Ile Ser Gly Ser Gly Gly Asn Thr
1               5

<210> SEQ ID NO 5
<211> LENGTH: 18
<212> TYPE: PRT
<213> ORGANISM: Artificial Sequence
<220> FEATURE:
<223> OTHER INFORMATION: R668 HCDR3

<400> SEQUENCE: 5

Ala Lys Asp Arg Leu Ser Ile Thr Ile Arg Pro Arg Tyr Tyr Gly Leu
1               5                   10                  15

Asp Val

<210> SEQ ID NO 6
<211> LENGTH: 11
<212> TYPE: PRT
<213> ORGANISM: Artificial Sequence
<220> FEATURE:
<223> OTHER INFORMATION: R668 LCDR1

<400> SEQUENCE: 6

Gln Ser Leu Leu Tyr Ser Ile Gly Tyr Asn Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: R668 LCDR2

<400> SEQUENCE: 7
```

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: R668 LCDR3

<400> SEQUENCE: 8

Met Gln Ala Leu Gln Thr Pro Tyr Thr
1               5

<210> SEQ ID NO 9
<211> LENGTH: 451
<212> TYPE: PRT
<213> ORGANISM: Artificial Sequence
<220> FEATURE:
<223> OTHER INFORMATION: R668 HC

<400> SEQUENCE: 9

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

```
Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450

<210> SEQ ID NO 10
<211> LENGTH: 219
<212> TYPE: PRT
<213> ORGANISM: Artificial Sequence
<220> FEATURE:
<223> OTHER INFORMATION: R668 LC

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
        195                 200                 205
Pro Val Thr Lys Ser Phe Asn Arg Gly Glu Cys
        210                 215

<210> SEQ ID NO 11
<211> LENGTH: 117
<212> TYPE: PRT
<213> ORGANISM: Artificial Sequence
<220> FEATURE:
<223> OTHER INFORMATION: R2810 HCVR

<400> SEQUENCE: 11

Glu Val Gln Leu Leu Glu Ser Gly Gly Val Leu Val Gln Pro Gly Gly
1               5                   10                  15
Ser Leu Arg Leu Ser Cys Ala Ala Ser Gly Phe Thr Phe Ser Asn Phe
            20                  25                  30
Gly Met Thr Trp Val Arg Gln Ala Pro Gly Lys Gly Leu Glu Trp Val
        35                  40                  45
Ser Gly Ile Ser Gly Gly Gly Arg Asp Thr Tyr Phe Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Lys Gly Glu Asp Thr Ala Val Tyr Tyr Cys
                85                  90                  95
Val Lys Trp Gly Asn Ile Tyr Phe Asp Tyr Trp Gly Gln Gly Thr Leu
            100                 105                 110
Val Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: R2810 LCVR

<400> SEQUENCE: 12

Asp Ile Gln Met Thr Gln Ser Pro Ser Ser Leu Ser Ala Ser Val Gly
1               5                   10                  15
Asp Ser Ile Thr Ile Thr Cys Arg Ala Ser Leu Ser Ile Asn Thr Phe
            20                  25                  30
Leu Asn Trp Tyr Gln Gln Lys Pro Gly Lys Ala Pro Asn Leu Leu Ile
        35                  40                  45
Tyr Ala Ala Ser Ser Leu His Gly Gly Val Pro Ser Arg Phe Ser Gly
    50                  55                  60
Ser Gly Ser Gly Thr Asp Phe Thr Leu Thr Ile Arg Thr Leu Gln Pro
65                  70                  75                  80
Glu Asp Phe Ala Thr Tyr Tyr Cys Gln Gln Ser Ser Asn Thr Pro Phe
                85                  90                  95
Thr Phe Gly Pro Gly Thr Val Val Asp Phe Arg
            100                 105

<210> SEQ ID NO 13
<211> LENGTH: 8
<212> TYPE: PRT
<213> ORGANISM: Artificial Sequence
<220> FEATURE:
<223> OTHER INFORMATION: R2810 HCDR1
```

```
<400> SEQUENCE: 13

Gly Phe Thr Phe Ser Asn Phe Gly
1               5

<210> SEQ ID NO 14
<211> LENGTH: 8
<212> TYPE: PRT
<213> ORGANISM: Artificial Sequence
<220> FEATURE:
<223> OTHER INFORMATION: R2810 HCDR2

<400> SEQUENCE: 14

Ile Ser Gly Gly Gly Arg Asp Thr
1               5

<210> SEQ ID NO 15
<211> LENGTH: 10
<212> TYPE: PRT
<213> ORGANISM: Artificial Sequence
<220> FEATURE:
<223> OTHER INFORMATION: R2810 HCDR3

<400> SEQUENCE: 15

Val Lys Trp Gly Asn Ile Tyr Phe Asp Tyr
1               5                   10

<210> SEQ ID NO 16
<211> LENGTH: 6
<212> TYPE: PRT
<213> ORGANISM: Artificial Sequence
<220> FEATURE:
<223> OTHER INFORMATION: R2810 LCDR1

<400> SEQUENCE: 16

Leu Ser Ile Asn Thr Phe
1               5

<210> SEQ ID NO 17
<211> LENGTH: 3
<212> TYPE: PRT
<213> ORGANISM: Artificial Sequence
<220> FEATURE:
<223> OTHER INFORMATION: R2810 LCDR2

<400> SEQUENCE: 17

Ala Ala Ser
1

<210> SEQ ID NO 18
<211> LENGTH: 9
<212> TYPE: PRT
<213> ORGANISM: Artificial Sequence
<220> FEATURE:
<223> OTHER INFORMATION: R2810 LCDR3

<400> SEQUENCE: 18

Gln Gln Ser Ser Asn Thr Pro Phe Thr
1               5

<210> SEQ ID NO 19
<211> LENGTH: 444
<212> TYPE: PRT
<213> ORGANISM: Artificial Sequence
<220> FEATURE:
<223> OTHER INFORMATION: R2810 HC
```

<400> SEQUENCE: 19

| | | | | | | | | | | | | | | |
|---|---|---|---|---|---|---|---|---|---|---|---|---|---|---|
| Glu | Val | Gln | Leu | Leu | Glu | Ser | Gly | Gly | Val | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asn | Phe |
| | | | 20 | | | | | 25 | | | | | 30 | | |
| Gly | Met | Thr | Trp | Val | Arg | Gln | Ala | Pro | Gly | Lys | Gly | Leu | Glu | Trp | Val |
| | | 35 | | | | | 40 | | | | | 45 | | | |
| Ser | Gly | Ile | Ser | Gly | Gly | Arg | Asp | Thr | Tyr | Phe | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Lys | Gly | Glu | Asp | Thr | Ala | Val | Tyr | Tyr | Cys |
| | | | | 85 | | | | | 90 | | | | | 95 | |
| Val | Lys | Trp | Gly | Asn | Ile | Tyr | Phe | Asp | Tyr | Trp | Gly | Gln | Gly | Thr | Leu |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | | 115 | | | | | 120 | | | | | 125 | | |
| Ala | Pro | Cys | Ser | Arg | Ser | Thr | Ser | Glu | Ser | Thr | Ala | Ala | Leu | Gly | Cys |
| | | 130 | | | | | 135 | | | | | 140 | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Lys | Thr | Tyr | Thr | Cys | Asn | Val | Asp | His | Lys | Pro | Ser | Asn |
| | | 195 | | | | | 200 | | | | | 205 | | | |
| Thr | Lys | Val | Asp | Lys | Arg | Val | Glu | Ser | Lys | Tyr | Gly | Pro | Pro | Cys | Pro |
| 210 | | | | | 215 | | | | | 220 | | | | | |
| Pro | Cys | Pro | Ala | Pro | Glu | Phe | Leu | Gly | Gly | Pro | Ser | Val | Phe | Leu | Phe |
| 225 | | | | 230 | | | | | 235 | | | | | 240 | |
| Pro | Pro | Lys | Pro | Lys | Asp | Thr | Leu | Met | Ile | Ser | Arg | Thr | Pro | Glu | Val |
| | | | 245 | | | | | 250 | | | | | 255 | | |
| Thr | Cys | Val | Val | Val | Asp | Val | Ser | Gln | Glu | Asp | Pro | Glu | Val | Gln | Phe |
| | | | 260 | | | | | 265 | | | | | 270 | | |
| Asn | Trp | Tyr | Val | Asp | Gly | Val | Glu | Val | His | Asn | Ala | Lys | Thr | Lys | Pro |
| | | 275 | | | | | 280 | | | | | 285 | | | |
| Arg | Glu | Glu | Gln | Phe | Asn | Ser | Thr | Tyr | Arg | Val | Val | Ser | Val | Leu | Thr |
| | 290 | | | | | 295 | | | | | 300 | | | | |
| Val | Leu | His | Gln | Asp | Trp | Leu | Asn | Gly | Lys | Glu | Tyr | Lys | Cys | Lys | Val |
| 305 | | | | | 310 | | | | | 315 | | | | | 320 |
| Ser | Asn | Lys | Gly | Leu | Pro | Ser | Ser | Ile | Glu | Lys | Thr | Ile | Ser | Lys | Ala |
| | | | | 325 | | | | | 330 | | | | | 335 | |
| Lys | Gly | Gln | Pro | Arg | Glu | Pro | Gln | Val | Tyr | Thr | Leu | Pro | Pro | Ser | Gln |
| | | | 340 | | | | | 345 | | | | | 350 | | |
| Glu | Glu | Met | Thr | Lys | Asn | Gln | Val | Ser | Leu | Thr | Cys | Leu | Val | Lys | Gly |
| | | | 355 | | | | | 360 | | | | | 365 | | |
| Phe | Tyr | Pro | Ser | Asp | Ile | Ala | Val | Glu | Trp | Glu | Ser | Asn | Gly | Gln | Pro |
| | | 370 | | | | | 375 | | | | | 380 | | | |
| Glu | Asn | Asn | Tyr | Lys | Thr | Thr | Pro | Pro | Val | Leu | Asp | Ser | Asp | Gly | Ser |
| 385 | | | | | 390 | | | | | 395 | | | | | 400 |
| Phe | Phe | Leu | Tyr | Ser | Arg | Leu | Thr | Val | Asp | Lys | Ser | Arg | Trp | Gln | Glu |
| | | | | 405 | | | | | 410 | | | | | 415 | |

```
Gly Asn Val Phe Ser Cys Ser Val Met His Glu Ala Leu His Asn His
                420                 425                 430
Tyr Thr Gln Lys Ser Leu Ser Leu Ser Leu Gly Lys
        435                 440
```

<210> SEQ ID NO 20
<211> LENGTH: 214
<212> TYPE: PRT
<213> ORGANISM: Artificial Sequence
<220> FEATURE:
<223> OTHER INFORMATION: R2810 LC

<400> SEQUENCE: 20

```
Asp Ile Gln Met Thr Gln Ser Pro Ser Ser Leu Ser Ala Ser Val Gly
1               5                   10                  15
Asp Ser Ile Thr Ile Thr Cys Arg Ala Ser Leu Ser Ile Asn Thr Phe
            20                  25                  30
Leu Asn Trp Tyr Gln Gln Lys Pro Gly Lys Ala Pro Asn Leu Leu Ile
        35                  40                  45
Tyr Ala Ala Ser Ser Leu His Gly Gly Val Pro Ser Arg Phe Ser Gly
    50                  55                  60
Ser Gly Ser Gly Thr Asp Phe Thr Leu Thr Ile Arg Thr Leu Gln Pro
65                  70                  75                  80
Glu Asp Phe Ala Thr Tyr Tyr Cys Gln Gln Ser Ser Asn Thr Pro Phe
                85                  90                  95
Thr Phe Gly Pro Gly Thr Val Val Asp Phe Arg Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 21
<211> LENGTH: 117
<212> TYPE: PRT
<213> ORGANISM: Artificial Sequence
<220> FEATURE:
<223> OTHER INFORMATION: R1103 HCVR

<400> SEQUENCE: 21

```
Glu Val Gln Leu Gln Gln Ser Gly Pro Glu Leu Val Lys Pro Gly Ala
1               5                   10                  15
Ser Val Arg Met Ser Cys Lys Ala Ser Gly Tyr Thr Phe Thr Asp Tyr
            20                  25                  30
Asn Ile His Trp Val Lys Gln Ser His Gly Lys Ser Leu Glu Trp Ile
        35                  40                  45
Gly Tyr Ile Tyr Pro Asn Asn Gly Asp Asn Gly Tyr Asn Gln Lys Phe
```

-continued

```
                50                  55                  60
Arg Gly Lys Ala Thr Leu Thr Val Asp Lys Ser Ser Thr Ala Tyr
65                  70                  75                  80

Met Glu Leu Arg Ser Leu Thr Ser Asp Ser Ala Val Tyr Tyr Cys
                85                  90                  95

Ala Arg Gly Arg Leu Arg Tyr Phe Asp Val Trp Gly Thr Gly Thr Thr
            100                 105                 110

Val Thr Val Ser Ser
        115

<210> SEQ ID NO 22
<211> LENGTH: 111
<212> TYPE: PRT
<213> ORGANISM: Artificial Sequence
<220> FEATURE:
<223> OTHER INFORMATION: R1103 LCVR

<400> SEQUENCE: 22

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly His Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Arg Thr Asp Phe Thr Leu Thr Leu Asp
65                  70                  75                  80

Pro Val Glu Ala Asp Asp Ala Ala Thr Tyr Tyr Cys Gln Gln Tyr Asn
                85                  90                  95

Glu Asp Pro Pro Thr Phe Gly Ser Gly Thr Lys Leu Glu Ile Lys
            100                 105                 110
```